United States Patent
Lalena et al.

(10) Patent No.: US 10,952,697 B2
(45) Date of Patent: Mar. 23, 2021

(54) SYSTEMS AND METHODS FOR CALIBRATING, CORRECTING AND PROCESSING IMAGES ON A RADIOGRAPHIC DETECTOR

(71) Applicant: CARESTREAM HEALTH, INC., Rochester, NY (US)

(72) Inventors: Michael C. Lalena, Webster, NY (US); Michael S. Means, West Henrietta, NY (US)

(73) Assignee: Carestream Health, Inc., Rochester, NY (US)

(*) Notice: Subject to any disclaimer, the term of this patent is extended or adjusted under 35 U.S.C. 154(b) by 25 days.

(21) Appl. No.: 16/383,751

(22) Filed: Apr. 15, 2019

(65) Prior Publication Data
US 2019/0231299 A1    Aug. 1, 2019

Related U.S. Application Data

(63) Continuation-in-part of application No. 15/041,153, filed on Feb. 11, 2016, now Pat. No. 10,285,663.
(Continued)

(51) Int. Cl.
*A61B 6/00* (2006.01)
*H04N 5/325* (2006.01)
(Continued)

(52) U.S. Cl.
CPC .......... *A61B 6/585* (2013.01); *A61B 6/4233* (2013.01); *A61B 6/4452* (2013.01);
(Continued)

(58) Field of Classification Search
CPC .......... A61B 6/00; A61B 6/582; A61B 6/585; A61B 6/423; A61B 6/4494; A61B 6/465; A61B 6/5205; A61B 6/548; A61B 6/563; A61B 6/56; A61B 6/4405; A61B 6/463; A61B 6/4452; A61B 6/467; A61B 6/4266; G01T 1/2928; G01T 1/2018; G01D 18/00; G01D 18/002; G01D 18/004;
(Continued)

(56) References Cited

U.S. PATENT DOCUMENTS 6,637,936 B2    10/2003    Crain et al.
7,298,825 B2    11/2007    Omernick et al.
(Continued)

FOREIGN PATENT DOCUMENTS

JP    10-201745    8/1998
JP    2004-188095    7/2004

OTHER PUBLICATIONS

International Search Report, Completed Jun. 28, 2012 for International Application No. PCT/US11/60335, 2 pages.
(Continued)

*Primary Examiner* — Jurie Yun

(57) ABSTRACT

A radiographic imaging system includes a radiographic detector having a scanning device to obtain patient identifying information. The detector is programmed to display the patient identifying information in human readable form and to access additional information about the patient stored in networked databases.

14 Claims, 16 Drawing Sheets

The touchscreen monitor has been integrated into the detector, combining detector, computer, & monitor in one.

Related U.S. Application Data which is a continuation of application No. 13/884,491, filed as application No. PCT/US2011/060335 on Nov. 11, 2011, now Pat. No. 9,289,184.

(60) Provisional application No. 61/414,176, filed on Nov. 16, 2010.

(51) Int. Cl.

| | | |
|---|---|---|
| *H04N 5/32* | (2006.01) | |
| *H04N 5/217* | (2011.01) | |
| *H04N 17/00* | (2006.01) | |
| *H04N 5/361* | (2011.01) | |
| *H04N 5/365* | (2011.01) | |

(52) U.S. Cl.
CPC ............ *A61B 6/4494* (2013.01); *A61B 6/465* (2013.01); *A61B 6/467* (2013.01); *A61B 6/5205* (2013.01); *A61B 6/548* (2013.01); *A61B 6/563* (2013.01); *A61B 6/582* (2013.01); *A61B 6/586* (2013.01); *H04N 5/2178* (2013.01); *H04N 5/32* (2013.01); *H04N 5/325* (2013.01); *H04N 5/361* (2013.01); *H04N 17/002* (2013.01); *A61B 6/4266* (2013.01); *A61B 6/4405* (2013.01); *A61B 6/463* (2013.01); *H04N 5/3651* (2013.01)

(58) Field of Classification Search
CPC ...... G01D 18/006; G01D 18/008; H05G 1/64; H04N 5/361; H04N 5/325; H04N 5/32; H04N 5/217; H04N 5/3651; H04N 5/2178; H04N 17/00; H04N 17/002
USPC .... 378/62, 63, 98, 98.2, 98.8, 116, 204, 207
See application file for complete search history.

(56) References Cited

U.S. PATENT DOCUMENTS

| | | |
|---|---|---|
| 7,483,557 B2 | 1/2009 | Takashi et al. |
| 7,519,156 B2 | 4/2009 | Marar |
| 7,684,544 B2 | 3/2010 | Wilson |
| 7,832,928 B2 | 11/2010 | Topfer et al. |
| 9,289,184 B2 | 3/2016 | Lalena et al. |
| 2006/0222146 A1 | 10/2006 | Spahn |
| 2007/0071166 A1 | 3/2007 | Spahn |
| 2010/0020933 A1 | 1/2010 | Topfer et al. |
| 2010/0185459 A1* | 7/2010 | Vera ................. A61B 6/5294 705/3 |

OTHER PUBLICATIONS

EP Partial Search Report dated Sep. 22, 2017 for EP Application No. 11 842 163.5 filed on Nov. 11, 2011, 2 pages.

Mary Couwenhoven et al., "Enhancement method that provides direct and independent control of fundamental attributes of image quality for radiographic imagery," Medical Imaging 2004: Visualization, Image-Guided Procedures and Display, Proceedings of SPIE vol. 5367, pp. 474-481.

J. Anthony Seibert et al., "Flat-field correction technique for digital detectors," Proc. SPIE vol. 3336, 1998, pp. 348-354.

J.P. Moy et al. "How does real offset and gain correction affect the DQE in images from x-ray flat detectors?," Proc. SPIE vol. 3659, 1999, pp. 90-97.

"Standard Practice for Manufacturing Characterization of Digital Detector Arrays," ASTM Standard E2597, 2008, 19 pages.

* cited by examiner

Detector acquires a new calibration image (flat field, dark image, phantom target image...)
1) Calibration Image is analyzed (with or without making use of other calibration data)
2) New calibration data is generated
3) New calibration data is merged with existing calibration data to create new calibration data.

The touchscreen monitor has been integrated into the detector, combining detector, computer, & monitor in one.

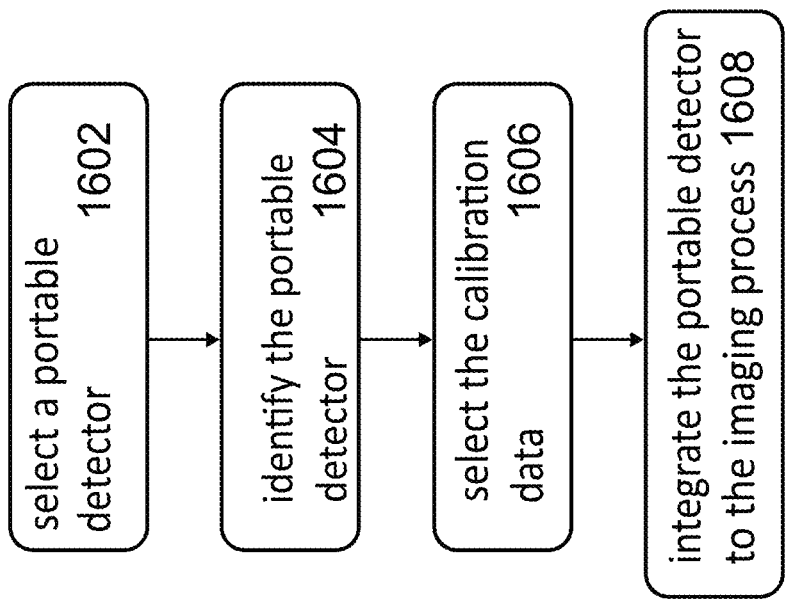

SYSTEMS AND METHODS FOR CALIBRATING, CORRECTING AND PROCESSING IMAGES ON A RADIOGRAPHIC DETECTOR

CROSS REFERENCE TO RELATED APPLICATIONS

This patent application is a continuation-in-part of U.S. patent application Ser. No. 15/041,153, filed Feb. 11, 2016, in the name of Lalena et al., entitled SYSTEMS AND METHODS FOR CALIBRATING, CORRECTING AND PROCESSING IMAGES ON A RADIOGRAPHIC DETECTOR, which is a continuation of U.S. patent application Ser. No. 13/884,491, filed May 30, 2013, in the name of Lalena et al., entitled SYSTEMS AND METHODS FOR CALIBRATING, CORRECTING AND PROCESSING IMAGES ON A RADIOGRAPHIC DETECTOR, which is a 371 national stage application of International Application No. PCT/US11/60335, filed Nov. 11, 2011, which itself claims benefit of commonly assigned, U.S. provisional patent application Ser. No. 61/414,176, filed Nov. 16, 2010, entitled "SYSTEMS AND METHODS FOR CALIBRATING AND PROCESSING IMAGES ON A RADIOGRAPHIC DETECTOR", in the name of Michael C. Lalena, the disclosure of which is incorporated herein by reference in its entirety.

FIELD OF THE INVENTION

The invention relates generally to the field of digital imaging, and in particular to medical digital imaging.

BACKGROUND

U.S. Pat. No. 7,298,825 titled PORTABLE DIGITAL DETECTOR SYSTEM directed to a detector for a portable imaging system wherein calibration data and configuration data from flash memory in the detector is transmitted to the portable imaging system.

U.S. Pat. No. 7,519,156 titled METHOD AND APPARATUS FOR HOT SWAPPING PORTABLE DETECTORS IN X-RAY SYSTEMS directed to a method for hot swapping a portable detector to an imaging system.

The article titled "Enhancement method that provides direct and independent control of fundamental attributes of image quality for radiographic imagery," by Mary Couwenhoven, Robert Senn, and David Foos.

SUMMARY

Accordingly, it is an aspect of this application to address in whole or in part, at least the foregoing and other deficiencies in the related art.

It is another aspect of this application to provide in whole or in part, at least the advantages described herein.

Another aspect of this application is to provide methods and/systems that can address exposure technique inconsistencies across multiple radiographic image processing systems.

Another aspect of this application is to provide methods and/systems that can reduce imaging workflow time to achieve presentation ready medical images at radiographic image systems.

Another aspect of this application is to provide methods and/systems that can perform calibration image processing (e.g., one or more calibrations and image corrections including but not limited to dark or offset calibration and correction, gain calibration and correction, defect identification and correction), additional image processing or all image processing at a digital detector of radiographic image systems.

Another aspect of this application is to provide methods and/systems that can perform file updates or calibration procedures that result in calibration files and/or information used in correcting subsequent raw radiographic image data at a radiographic detector.

Another aspect of this application is to provide methods and/systems that includes a display at a digital radiographic flat panel detector (DR FPD) that can display patient identifying information and captured radiographic images, images processed for presentation to the user in a common standard format such as DICOM (Digital Imaging and Communications in Medicine standard for distributing and viewing any kind of medical image from a server regardless of the origin) at digital detectors (e.g., wireless DR FPD) of radiographic image systems. Exemplary detectors can retrieve or export such images to a host radiographic imaging system using patient identifying information.

Another aspect of this application is to provide methods and/systems that can store technique information for each view at a digital detector for radiographic image systems.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 16 is a flowchart that shows an exemplary method embodiment for calibrating a new portable detector according to an embodiment of the application.

DESCRIPTION OF EXEMPLARY EMBODIMENTS

Figure 1:
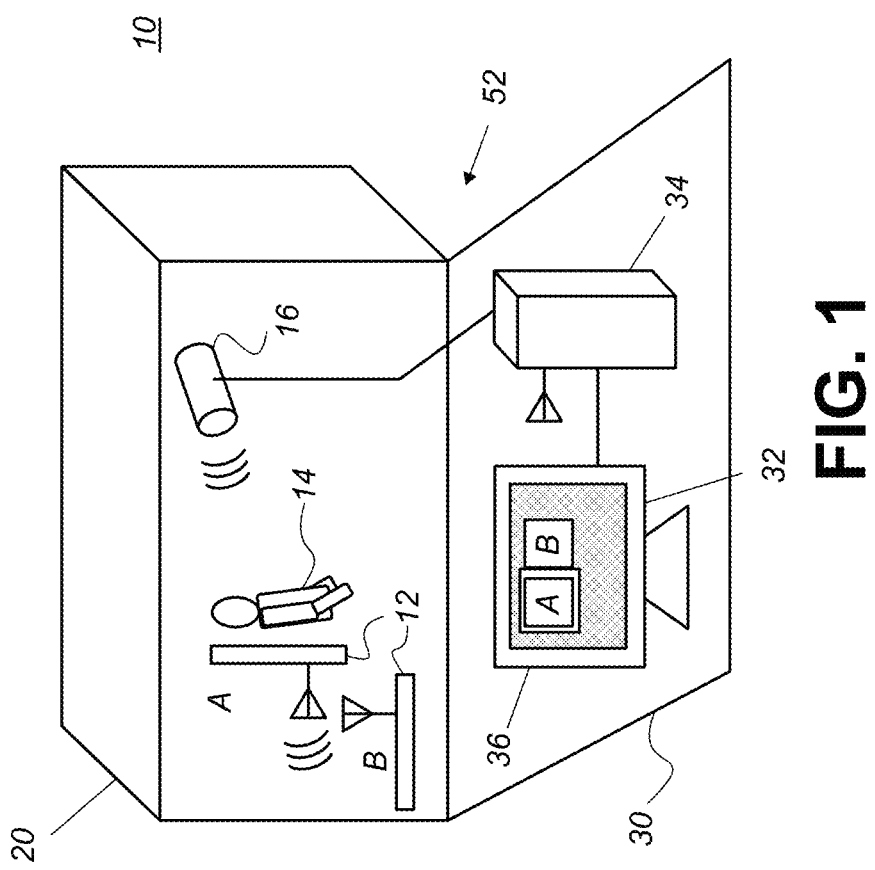
FIG. 1 is a block diagram showing an x-ray imaging room having two portable DR receiver panels according to an embodiment of the application.

The following is a detailed description of exemplary embodiments of the invention, reference being made to the drawings in which the same reference numerals identify the same elements of structure in each of the several figures.

In the field of radiography for the purpose of medical diagnosis, a radiography system has been widely known in which a subject is subjected to radiation to detect the distribution of radiation rays transmitted through the subject, thereby obtaining a radiographic image of the subject. In related art radiography systems, a digital radiographic (DR) detector (e.g., flat panel detector having a thin and flat panel-like shape) in which a great number of photoelectric transducers are arranged in a matrix manner has been developed and used. In DR detectors, radiation rays transmitted through the subject are subjected to photoelectric conversion to provide an electronic signal as image information. The image information generated by the DR detector is subjected to image processing, thereby providing a radiographic image (e.g., medical digital images) of the subject in a timely manner.

Certain exemplary embodiments herein can subject image information (e.g., X-ray image data, calibration-corrected image data) generated by a DR detector to image processing to result in a useful desired medical digital image. Exemplary image processing can subjects the X-ray image data to processes such as, but not limited to compensation processing, expansion/compression processing, space filtering processing, recursive processing, gradation processing, scattering radiation compensation processing, grid compensation processing, frequency enhancement processing, or dynamic range compression processing, and the like (e.g., individually or in various combinations).

Embodiments of radiographic systems can include an x-ray source assembly, a controller, and a detector attached to a radiographic system (e.g., mobile radiographic imaging system). Through device and method embodiments according to the application, exemplary processes of installing and operating a DR detector to process images are described.

FIG. 1 is a diagram that shows an embodiment of an x-ray imaging room. As shown in FIG. 1, there is an x-ray imaging room 10 that can include an X-ray apparatus 52 that uses a plurality of wireless DR receiver panels 12, (two panels 12 are shown, one labeled A, the other labeled B). Each DR receiver panel 12 can include an integrated controller/CPU as known in the art to control operations thereof. Each DR receiver panel 12 has a unique identifier such as identifying serial number or other encoding, typically assigned at time of manufacture. The wireless transmission protocol can use this unique encoding as a "signature" for distinguishing between any two or more DR receiver panels 12 from the same or manufacturer or different manufacturers and for setting up the proper communication channel between the panel and a controller 34 (e.g., of the apparatus 52).

As shown in FIG. 1, X-ray imaging room 10 has an imaging room 20, which can be a shielded area where a patient 14 is imaged and contains an x-ray source 16, and a control room 30 that can include a display 32 and controller 34 for communicating with DR receiver panels 12 over an interface (e.g., wired, RF, IR or wireless) and that contains control logic for executing known functions with a selected DR receiver panel 12. In the embodiment shown in FIG. 1, the image is obtained on the active DR receiver panel 12 labeled A; the DR receiver panel labeled B is inactive, not currently being used. An operator interface 36 accepts operator instructions such as to select a DR receiver panel, to communicate with the active DR receiver panel 12 labeled A, and control operations for obtaining a selected image of the patient 14. In the embodiment shown, display 32 is a touch screen display, enabling the operator or technologist to easily control the X-ray imaging room 10 and select either the A or the B DR receiver panel 12 as the active DR receiver panel for obtaining the radiographic image using a graphical user interface (GUI).

Figure 2:
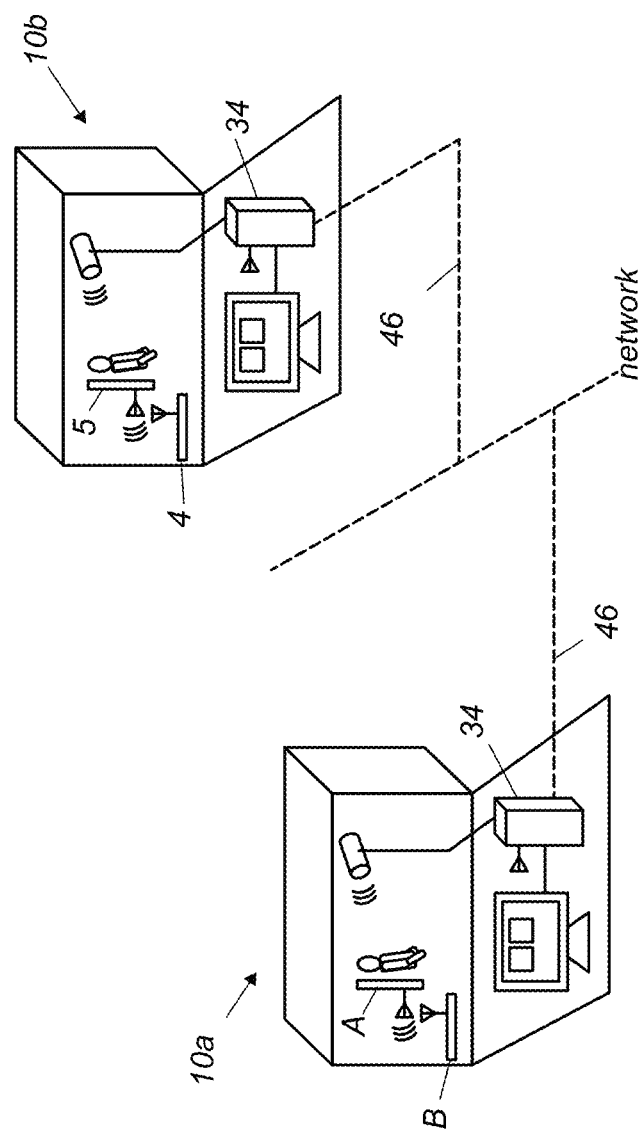
FIG. 2 is a block diagram showing a portion of a hospital or other facility having multiple x-ray imaging rooms that use DR receiver panels according to an embodiment of the application.

FIG. 2 is a diagram that shows a facility or department including a plurality of imaging rooms. As shown in FIG. 2, imaging room 10a has two designated DR receiver panels 12, labeled A and B. Imaging room 10b has two designated DR receiver panels, labeled 4 and 5. The DR receiver panels 12 generally remain at their respective rooms 10a or 10b. However, in the hospital environment, a crisis situation, a scheduling difficulty, or an equipment maintenance need can occur, requiring one room to borrow a DR receiver panel 12 that was originally designated for another room. For example, a detector failure condition may require that one or both of the DR receiver panels 12 at x-ray imaging room 10b be temporarily out of commission. A technologist may then remove one of the DR receiver panels 12 from x-ray imaging room 10a in order to handle such a temporary emergency. In such events, calibration can be required either because of changes of the detector panels 12, changes of the x-ray imaging room 10, movement of the detector panels 12 to a different x-ray source 16/imaging room or for image quality (IQ) requirements, and this new calibration data can be stored in memory of the detector panels 12 or transferred back to the detector panels 12 from the controller 34 over network 46 for storage to ensure that the calibration data on the detector panels 12 is refreshed. As a backup, the entire calibration and configuration data can be uploaded to the imaging room 10 (e.g., the controller 34) or a networked location based on the identity of the detector panels 12.

The term calibration includes but is not limited to typical elements of the detector flat-field calibration known in the art (James A. Seibert, John M. Boone, and Karen K. Lindfors in "Flat-field correction technique for digital detectors," *Proc. SPIE Vol.* 3336, 1998, p. 348-354; by Jean-Pierre Moy and B. Basset in "Flow does real offset and gain correction affect the DQE in images from x-ray flat detectors?" *Proc. SPIE*, 3659, 1999, pp. 90-97). The most basic calibration and correction algorithms generally include 3 steps. First, the dark signal of the detector (that is, the signal in the absence of any X-ray exposure) is obtained. Pixel by pixel variations in the dark signal of the detector are characterized to form a dark or offset map containing the dark variations. The offset map is then subtracted from the X-ray exposure in a process termed dark or offset correction. Second, the variations in the sensitivity of the pixels are characterized. This is done by capturing one or more flat field exposures, which are then offset-corrected. The resulting image is the gain map. In the gain correction step, the offset-corrected X-ray exposure is divided by the gain map. Finally, defective pixels in the image are removed by interpolating their values from neighboring good pixels. Ideally this three-step procedure compensates for any fixed pattern noise introduced by the detector. In portable detectors additional offset corrections may be necessary, such as those described in U.S. Pat. No. 7,832,928B2 "Dark correction for digital X-ray detector" by K. Töpfer, R. T. Scott and J. W. Dehority.

Figure 3:
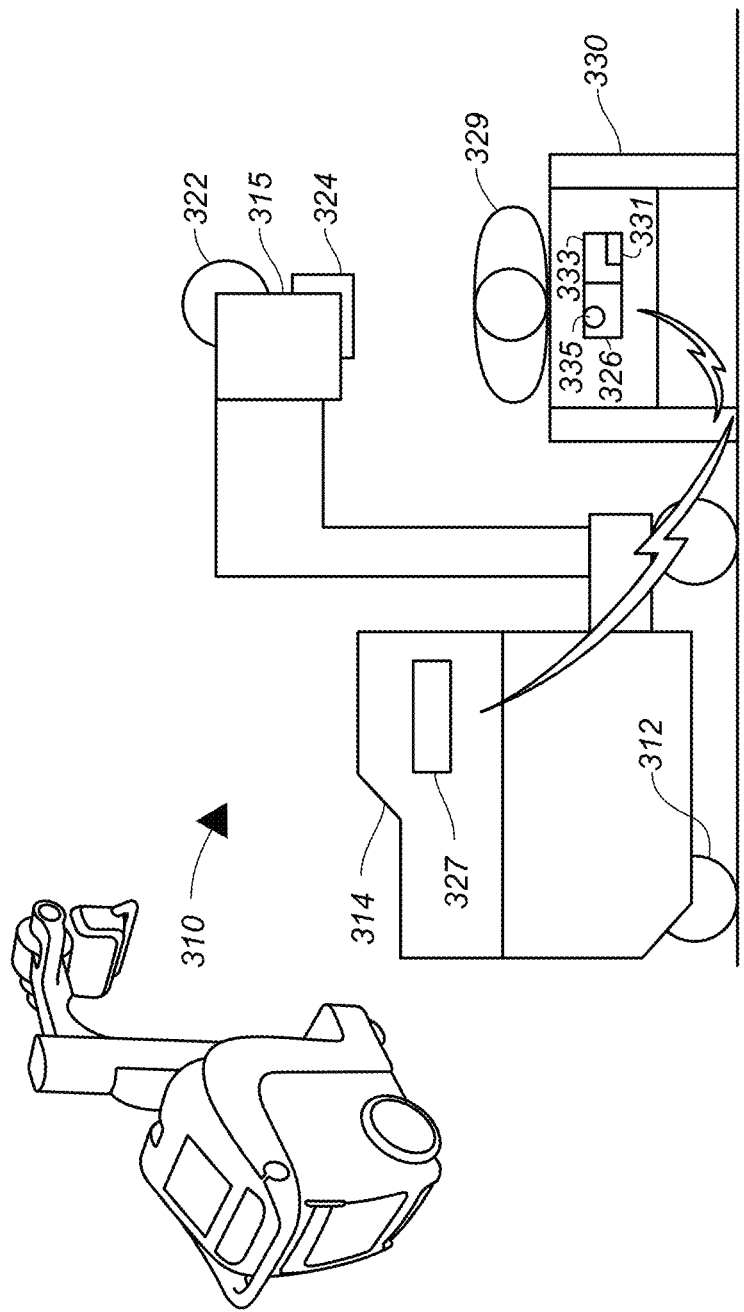
FIG. 3 is a diagram that shows a mobile x-ray system according to an embodiment of the application.

Also used within an imaging room or as a stand alone capability, a mobile radiography (e.g., x-ray) imaging system can incorporate DR receiver panels such as DR receiver panels 12. FIG. 3 is a diagram that shows an embodiment of a mobile x-ray system according to the application.

As shown in FIG. 3, a mobile radiography or x-ray scanning system 310 includes a wheeled base 312, an operator console 314, and an x-ray source assembly 315. The x-ray source assembly 315 can include an x-ray tube housing 322 containing an x-ray source, the tube housing 322 having an x-ray emission aperture (not shown), and a collimator 324 can be attached to the tube housing 322 and aligned with the x-ray emission aperture. The scanning system 310 is embodied for scanning an object 329 to be imaged, illustrated on a table 330.

The mobile x-ray scanning system 310 further can include a controller 327 (e.g., imaging computer) and a removable radiographic detector 326 in communication with the controller 327. FIG. 3 illustrates the controller 327 communicating wirelessly with the detector 326 as the detector 326 is activated and brought in a vicinity of the controller 327. The detector 326 can include the supplemental capability for wired or tethered communication to the controller 327.

In accordance with one embodiment, a detector platform, such as the portable detector platform 326, includes memory 331, which can be loaded from the vendor with a full set of configuration parameters and calibration files. This full set of configuration parameters and calibration files for the detector 326 can be used with the mobile x-ray scanning system 310 based on the unique identifier (e.g., MAC address or serial number) when the detector 326 is connected or after the detector 326 is re-connected. The data included in the memory 331 can include all or a subset of calibration data, model information and component configuration data. The memory 331 can include one or more of cache, ROM, PROM, EPROM, EEPROM, flash, SRAM, non-volatile memory (NVM), flash memory and be ROM or RAM within the controller 327 or removable memory that is removably connected to the detector 326 or controller 327.

In accordance exemplary embodiments, if during system operations, calibration is required either because of changes of the detector 326, changes of the mobile x-ray imaging system 310, movement of the detector 326 to a different imaging system (e.g., 310)/imaging room or for image quality (IQ) requirements, this new calibration data can be stored in the memory 331 or transferred back to the detector 326 from the controller 327 for storage for ensuring that the data on the detector 326 is refreshed. As a backup, the entire calibration and configuration data can be uploaded to the mobile x-ray imaging system 310 (e.g., the system controller 327) or a networked location based on the detector 326 identity. Some updated calibration data such as dark image calibration update can be determined and directly stored at the detector 326. Other updated calibration data such as imaging system configuration data when the detector 326 is moved to a different imaging system/imaging room can be transmitted to the detector 326.

As shown in FIG. 3, the detector 326 can include the transmit/receive unit 335 for communicating with the controller 327. The transmit/receive unit 335 can wirelessly connect to the controller 327 or to another part of the mobile x-ray imaging system 310. The detector 326 can include a detector controller 333 receiving and processing signals from the controller 327 and controlling functions of the detector 326, including configuring the detector 326 for use with the particular imaging system 310.

Each digital detector may need to be calibrated. Currently, a digital file can be included with each digital detector that includes factory calibration files. The file can be included on media such as a DVD, CD, USB drive, or other media for storing digital information. Alternatively, the file can be stored at the detector 326 (e.g., memory 331).

Each digital detector may also require supplemental (e.g., periodic) calibration to be performed (e.g., at the customer site). Supplemental calibration can include periodic calibration such as, but not limited to calibration based on the number of images exposed by a detector, time based periodic or aperiodic calibration such as operator imitated, repeated or event based calibration like dropping the detector. Calibration data can comprise any one of captured raw calibration image, correction images or maps generated from one of more calibration images (examples include gain, offset, defect and lag maps) or other non-image calibration data, such as temperature, radiographic technique and generator prep time.

It is desired to use detectors with many exam rooms/computers without having to download calibration files or recalibrate the digital detector at the computer for each exam room. It is desirable to store these calibration files in non-volatile flash memory on the detector itself and make use of the calibration files on the detector without needing to download them to a computer.

One exemplary method can include the following steps.

A radiographic detector stores factory calibration data at the detector (e.g., non-volatile flash memory or similar) and then uses that calibration data to correct the image before transferring it to the imaging system.

The calibration data is stored at the detector (e.g., at a storage device, ROM, RAM) on removable flash memory. The data storage does not need to be removable but can be on internal or permanent memory. The storage device or removable flash memory would preferably be a secondary storage. Further, the removable memory can also be used as a backup to fixed storage on detector or as a mechanism for backups to the console/imaging system PC or elsewhere or as a mechanism for loads from the console/imaging system PC or elsewhere.

The removable flash memory can also be used to upload calibration data to the detector from the imaging system. The calibration data can stay on the removable flash memory or be copied to internal flash memory.

Exemplary embodiments can store other calibration data at the detector. For example, store periodic (Daily, Weekly, Monthly, Yearly), dark, flat field calibration, and phantom target files at the detector (e.g., at the detector, internal memory or removable flash) along with the factory calibration and automatically correcting images also using that other calibration data at the detector.

Optionally calibration data (e.g., captured calibration images) and the correction image (e.g., data to be applied to a new x-ray image to correct its raw image data) can be stored separately at the detector. The correction images, such as gain, defect and offset maps, represent a combination of multiple calibration raw images based on some pre-defined image processing and can be the only data that preferably is stored in high speed RAM. The predefined image processing can include simple operations, such as subtraction of dark images and averaging of multiple exposures, as in the case of a gain map, or more complicated operations such as spatial frequency filtering, statistical analysis and thresholding as described for defect maps in "Standard Practice for Manufacturing Characterization of Digital Detector Arrays", ASTM Standard E 2597 (2008). Detector preferably updates the correction image every time a new calibration is performed. Pre-merging the factory and periodic calibration data can allow for a faster preview time and/or can reduce the amount of high speed RAM (vs. flash memory) required at the detector.

Any periodic dark calibrations are preferably automatically performed by the detector when desired or necessary. For example, if the detector attempts to perform a dark calibration every 12 hours for a required daily (24 hours) dark calibration. However, should the detector be unable to perform the required dark calibration within the required time (24 hours), the detector can perform the required dark correction later, when possible. In one embodiment, the detector itself can determine if/when to perform this calibration on its own. For example, the detector can wait until a prescribed time (e.g., an hour) has passed without being used to initiate the periodic dark calibration. Alternatively, the detector can initiate the periodic dark calibration upon completion of an exposure series or examination. Further, even when a detector initiated dark calibration is in process, an incoming request (e.g., from an operator) to receive incident radiation or generate an image of a subject can interrupt the detector initiated dark calibration.

Allow users to register (and e.g., select/activate) the detector by attaching/connecting the detector into the imaging system or by selecting the detector from a list of available wireless detectors. Various mechanisms such as wireless technology (e.g., WiFi, bluetooth, zigbee, etc.), or a Bar Code, RF-ID can be used to indicate desire to register a detector. Any necessary or desirable information can be transferred from the radiographic detector to the imaging system when the detector is connected, or subsequently. For example, a unique ID, Serial #, IP Address, Name, Detector Type, width/height in mm, width/height in pixels, scintillator type (e.g., gadolinium oxisulfide, cesium iodide) can be automatically communicated, communicated upon request or subsequently communicated.

Certain exemplary apparatus and/or method embodiments can perform image processing (e.g., partial image processing, "DICOM image processing, display ready image processing, complete image processing, etc.) at the detector. The result of this type of processing is an image ready to be viewed by the user for medical diagnosis, detection of objects and other purposes.

To perform the image processing at the detector, the detector can store the image processing parameters in memory (e.g., non-volatile flash memory). If the image processing parameters are view based, this would include saving the processing data for each view (e.g., body part, projection, position combination or combination thereof). Alternatively, in one embodiment, a single image processing can be used on all views.

Exemplary embodiments can store technique information for each view at the detector. This capability can address having inconsistent techniques at different DR systems.

The detector can store the same information (e.g., first technique information) backed up and restored to transfer view information, image processing parameters and techniques from one machine/image processor/imaging system to another. The detector stores the data. This allows for the transfer of information to and from the detector and imaging system or from the detector among multiple radiographic imaging systems. For example, an embodiment of a detector can include technique information for at least one view is moved between different radiographic imaging systems, technique information for at least one view can be transferred from a first imaging system to a second different (e.g., and a third still different) imaging system.

The detector can automatically synchronize the image processing and the technique information with an imaging system when the detector is connected (and/or hot swap) or registered to the imaging system.

The detector can also supply the computer/generator of an imaging system with image processing and technique information on demand (e.g., operator initiated) for specific view(s).

Since the detector is correcting and processing the images, image preview time may be affected. The detector can transmit multiple copies of the same image to the imaging system: raw, corrected, and processed (e.g., presentation ready) to improve preview times. Further, full, partial, sub-sampled, or preview versions of each (e.g., raw, calibration-corrected, and processed) can be sent. Image transmission (e.g., network w/direct memory access (DMA)) would not slow down the image processing. For example, one row of data can be transmitted with a different (e.g., next row) can be image processed.

With the detector now able to produce fully processed image data, an operator can attach directly/wirelessly connect a computer monitor into the detector. For example, the detector would have a connector for a DVI, HDMI, mini-HDMI, Display Port, prescribed connector, customized connector or mini-Display Port cable. Further, remote desktop technology can allow using a network port for a remote monitor. Alternatively, a web application driven over a network hosted by a web server on the detector can be used.

Exemplary embodiments can allow for the integration of a flat panel display directly to the detector and allow the operator to view the image directly at the detector. While this may not be employed at a typical hospital, it may be employed at military applications as it may eliminate the need for the laptop used in a battlefield environment.

The display can be a touch screen display that drives a fully capable computer similar to existing DR imaging system applications and/or DR imaging applications.

This display can be embedded in the detector itself. For example, the display comprises the backside (or a portion thereof) of the detector.

In one embodiment, a display at the detector is not a full featured display. For example, the detector display can be a low cost or small display on the detector for simple diagnostics. A technician may not be able to evaluate images with small display, but can at least look at the image and verify the image was acquired. Further, the technician can perform simple or limited functionality from a limited feature display (e.g., not touch screen enabled) like sync calibrations, view image, send images, etc.

Exemplary embodiments can provide a detector that can produce and export DICOM images (e.g., image data with a patient/exam information header). Thus, the detector can be integrated with DICOM archives, DICOM printers and/or DICOM servers. In one embodiment, the detector can receive examination records from a DICOM Modality Worklist.

If the detector does have a removable flash drive (for exporting calibration data) then this can also be used to export images. This could be used to retrieve images if there is a networking problem.

In certain exemplary embodiments, a detector can be employed for X-ray, ultrasound, patient monitoring applications, fluoroscopy or tomosynthesis.

Figure 15:
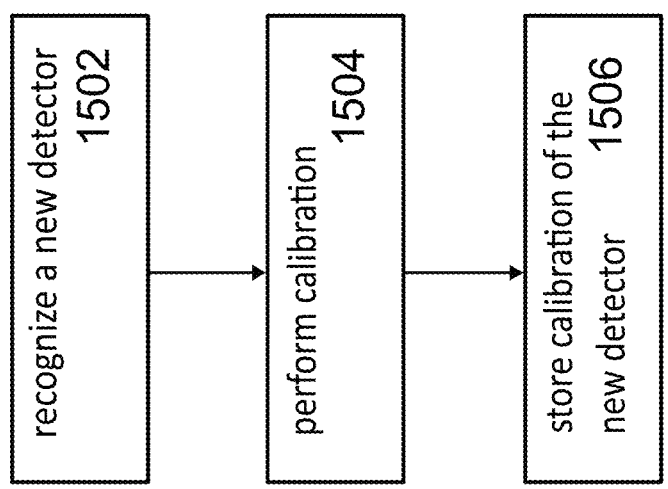
FIG. 15 is a flowchart that shows an exemplary method embodiment for calibrating a new portable detector according to an embodiment of the application.

A method embodiment for calibrating a new portable detector will now be described that can address imaging system access to calibration information for any radiographic detector that needs to be used. An exemplary method shown in FIG. 15 can include action 1502 for recognizing a new detector, action 1504 for performing a calibration, and action 1506 for storing the calibration of the new detector.

In action a 1502 new detector is recognized. At this point, a unique identifier such as serial number is read by the calibration host. In the alternative when an internal or institutional identifier is preferred, the host can assign such an identifier to the new detector. A site assigned unique ID can be an IP Address or Name. In yet another alternative, a MAC address can be assigned to the new detector. Regardless of the identifier selected or assigned, the new detector is known or identified by that designation and can be tracked through the network.

In action 1504, the new detector can be calibrated for all systems. The calibration procedure is administered and calibration data is generated for the new detector with respect to gain, offset and defect and compensation, and other aspects that may need to be compensated in the images, for example lag, the image retention from previous frames. However, since detector is operable with different systems the detector can be calibrated to all known imaging systems that can use the detector. In the alternative, since detector is operable with different imaging system types (e.g., radiographic sources, x-ray generators), the detector can be calibrated to all known imaging system types that can use the detector. In yet another alternative, the detector can be calibrated to a subset of likely imaging systems or types of imaging system that will likely use the detector.

In action 1506, the calibration information can be stored. In a network environment there are a myriad of places where the calibration information can be stored. For example, the calibration can be stored in the detector such as detector 12 or detector 326 and every time the detector is used by an imaging system, the detector can incorporate/use the calibration data for the imaging operation. In the alternative, the calibration data can be propagated to all the imaging systems. In this example, when a detector is coupled to an imaging system, all the host has to do is select the calibration data for the detector from its internal memory and transfer the calibration data to the detector. The calibration data can be selected based on (e.g., indexed by the unique identifier) the respective portable detector.

Upon completion of the calibration procedure (action 1504), calibration information (e.g., updated calibration information) for the detector is complete. The calibration maps are the applied to correct subsequent raw radiographic image data. We refer to the result of the operation as "calibration-corrected image" data. If all corrections are applied, i.e., for gain, offset and defect, the result is a fully "flat-field" corrected image. However, certain exemplary embodiments herein perfonn one or more of a single calibration correction, a subset of calibration corrections or all calibration correction processing at the radiographic detector, where at least one copy of the calibration information is stored. Therefore the term "calibration-corrected" image refers to this more general case. A calibration-corrected image could simply have offset corrections applied on the detector.

An embodiment of a method of integrating a portable detector to an imaging system will now be described that can follow a procedure for hot swapping a new radiographic detector to an imaging system (e.g., imaging system 10) in the event that the current detector is not functioning within tolerances. A detector may be out of tolerance when the battery is below a certain level, when the temperature exceeds a threshold, or when the detector fails to operate within acceptable levels. The terms hot swap, hot insertion, or plug-and-play are conveniently used to refer to the exchange or insertion of portable detectors (e.g., 12, 326) into the imaging process so as to allow the imaging system (e.g., 10) to function immediately after the swapping or insertion process takes place. An exemplary method, shown in FIG. 16, can address the need in the art for easy integration of portable detectors through calibration data sharing. The exemplary method of FIG. 16 includes selecting a portable detector 1602, identification of the portable detector 1604, selecting the calibration data 1606, and integrating the portable detector to the imaging process 1608.

In action 1602, a portable detector is selected. The portable detector (e.g., detector 12 or detector 326) can be any detector capable of exchanging information with the imaging system (e.g., imaging system 10 or imaging system 310) using a well defined protocol such as docking protocol or wireless protocol.

Figure 9:
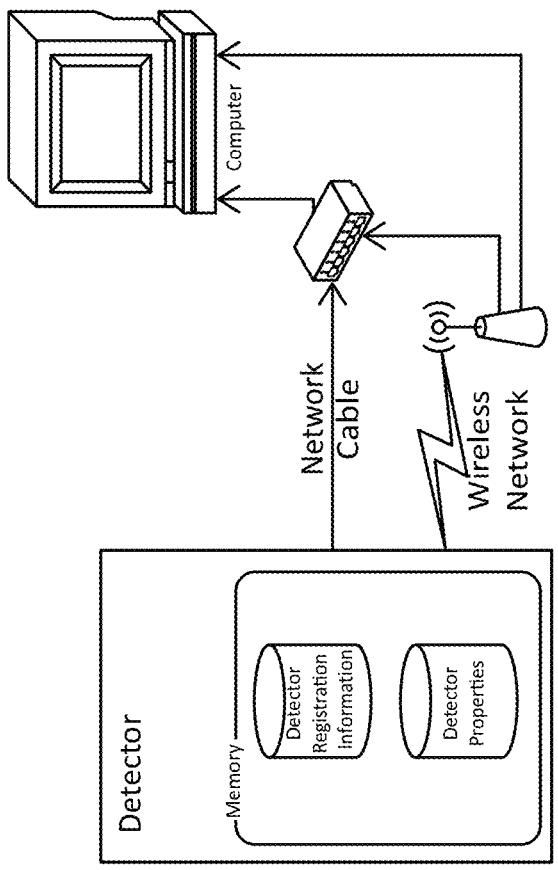
FIG. 9 is a diagram that shows an exemplary digital detector to transfer registration information (e.g., manually) to an x-ray imaging apparatus upon connection in accordance with the application.

In action 1604, the host or imaging system identifies the detector using the defined protocol. The system then proceeds to read the identification from the detector. The detector receives the identification of the imaging system. FIG. 9 is a diagram that shows an exemplary digital detector to transfer registration information (e.g., manually) to an x-ray imaging apparatus upon connection.

In action 1606, the calibration data is selected or updated for the portable detector. The calibration data can be unique for that detector or the detector imaging system pair.

In one embodiment, the host can look up the stored calibration data for the given detector and transmit the calibration to the detector for use in imaging operations. In the alternative, the detector can select among the stored calibration data (e.g., stored at the detector) the corresponding calibration data for the specific imaging system, imaging system type or imaging system/detector pair.

In one embodiment, storing and using calibration data can include storing and using by imaging system type. For example, the unique identifier of the imaging system can be used as the index key of a table for reading the calibration data stored at the detector.

In action 1608, the imaging system can use the identification data to integrate the detector to the imaging process of the imaging system. The detector can use the selected calibration data at the detector to correct raw electronic image data and transfer the same (e.g., at least partially calibration corrected image data/image) to the imaging system in imaging operations.

In an alternative embodiment, the calibration data, can be transferred to an external processor from the detector, and subsequent image data can be transferred and corrected externally to the detector and the imaging system. Preferably, the calibration corrected image data and/or presentation ready image is then transferred back to the imaging system.

In one embodiment, up to three DR receiver panels 12 can be registered with a radiographic imaging system, however, generally one DR panel is active. A registered DR receiver panel has communicated calibration and configuration data as needed with the radiographic imaging system. Certain exemplary embodiments of detectors herein can capture x-ray radiation as a. receptor.

Figure 4:
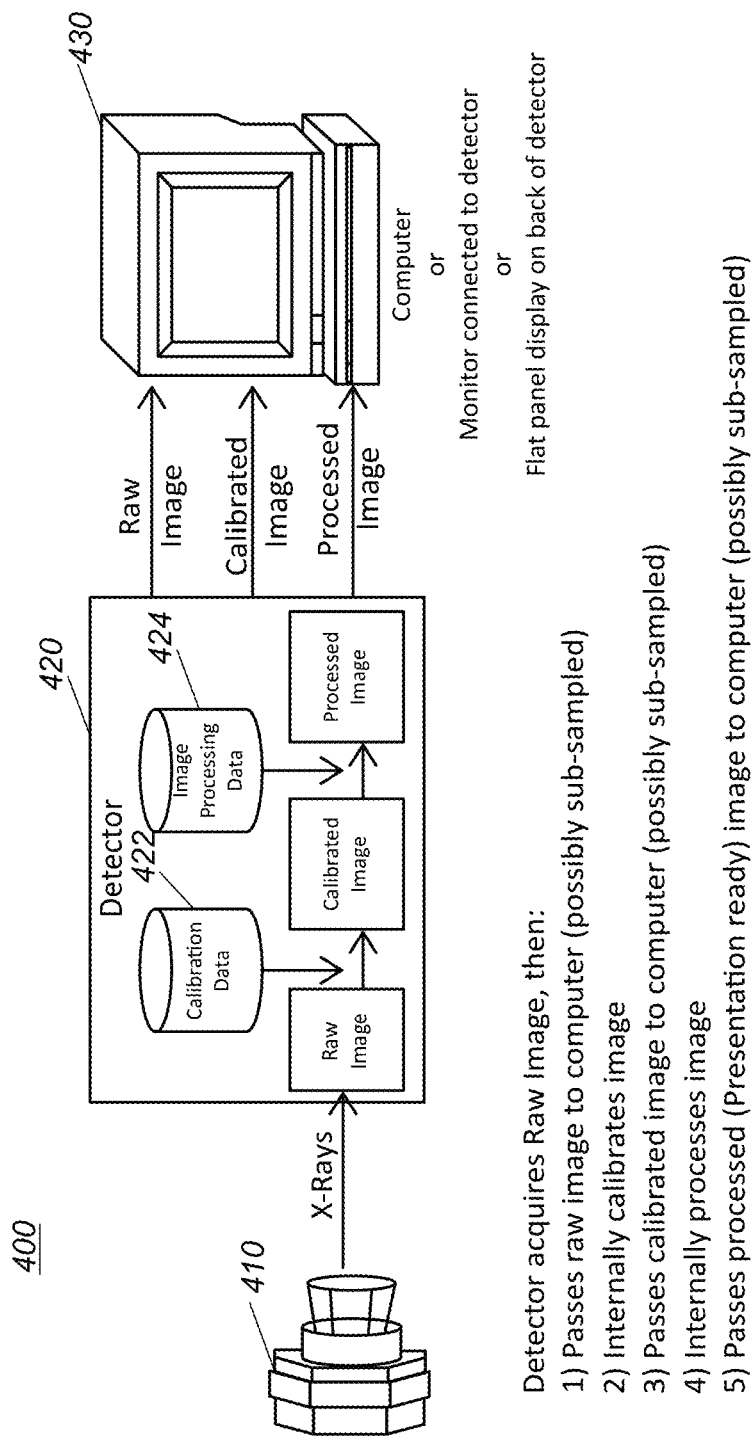
FIG. 4 is a diagram that shows an exemplary digital detector to process data at the digital detector for use in an x-ray imaging apparatus in accordance with the application.

FIG. 4 is a diagram that shows an exemplary digital detector to process data at the digital detector for use in an x-ray imaging apparatus in accordance with the application. As shown in FIG. 4, an x-ray imaging apparatus 400 can include an x-ray source 410 that can emit x-rays toward an object and a detector 420 can include a matrix of pixels to detect an image of x-rays having passed though the object. As shown in FIG. 4, embodiments of a detector 410 can pass raw image data (e.g., sub-sampled), calibration corrected image data or processed imaged data ready for viewing to a display 430. The display 430 can include, but is not intended to be limited to a computer (e.g., of a console of a radiographic imaging system), a monitor or a flat panel display on a non-imaging side of the detector. To provide calibration corrected image data, the detector 420 can include calibration data 422. To provide processed imaged data, the detector 420 can include image processing data 424.

Figure 5:
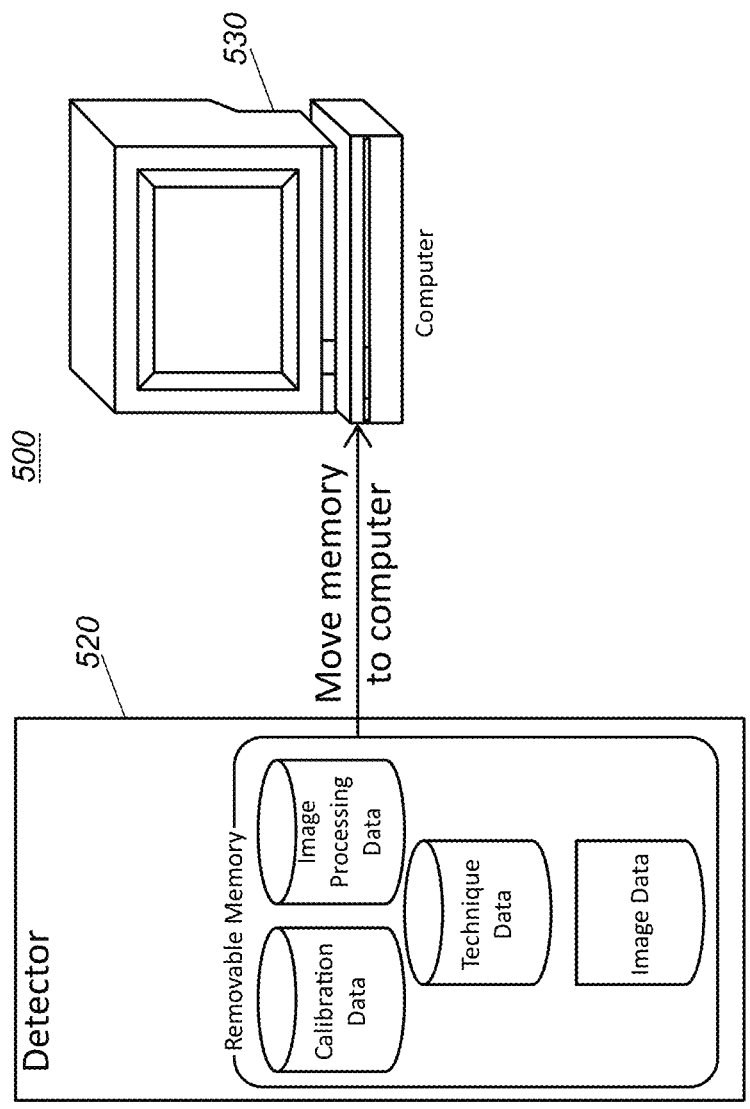
FIG. 5 is a diagram that shows an exemplary digital detector to include removable memory to transfer data, raw images or processed images for use in an x-ray imaging apparatus in accordance with the application.

FIG. 5 is a diagram that shows an exemplary digital detector to include removable memory to transfer data, raw images or processed images for use in an x-ray imaging apparatus in accordance with the application. As shown in FIG. 5, an x-ray imaging apparatus 500 can include an x-ray detector 520 can include a matrix of pixels to detect an image of x-rays having passed though an object and a computer 530 (e.g., console) in a radiographic imaging system (not shown). The detector 520 and the computer 530 can exchange or transfer calibration, image processing and/or technique data, acquired images and the like by using a removable memory card, storage device wireless or wired connection. A transferable memory device can be used in the case of network failure.

Figure 6:
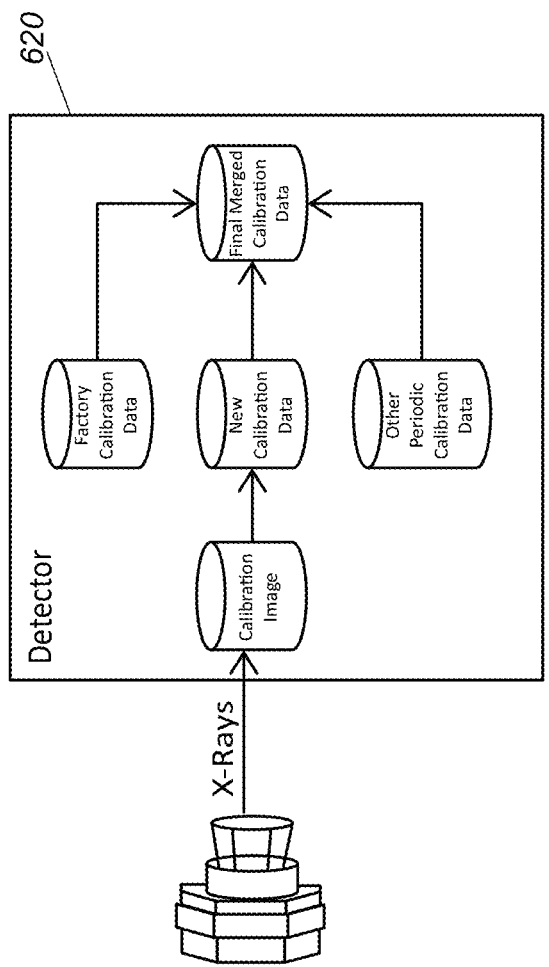
FIG. 6 is a diagram that shows an exemplary digital detector to receive additional calibration data at the digital detector for use in an x-ray imaging apparatus in accordance with the application.

FIG. 6 is a diagram that shows an exemplary digital detector embodiment that is capable of storing, using, creating and/or merging various calibration data at the digital detector. As shown in FIG. 6, a radiographic detector 620 can acquire new calibration image (e.g., flat field, dark image, phantom target image, etc.). The new calibration image can be used to generate new or additional calibration data. Further, the new calibration data can be merged with other calibration data such as but not limited to factory calibration data or other periodic calibration data to result in a set of or single merged calibration data. In one embodiment, the new calibration data and/or the merged calibration data can be made at the detector 620.

Figure 7:
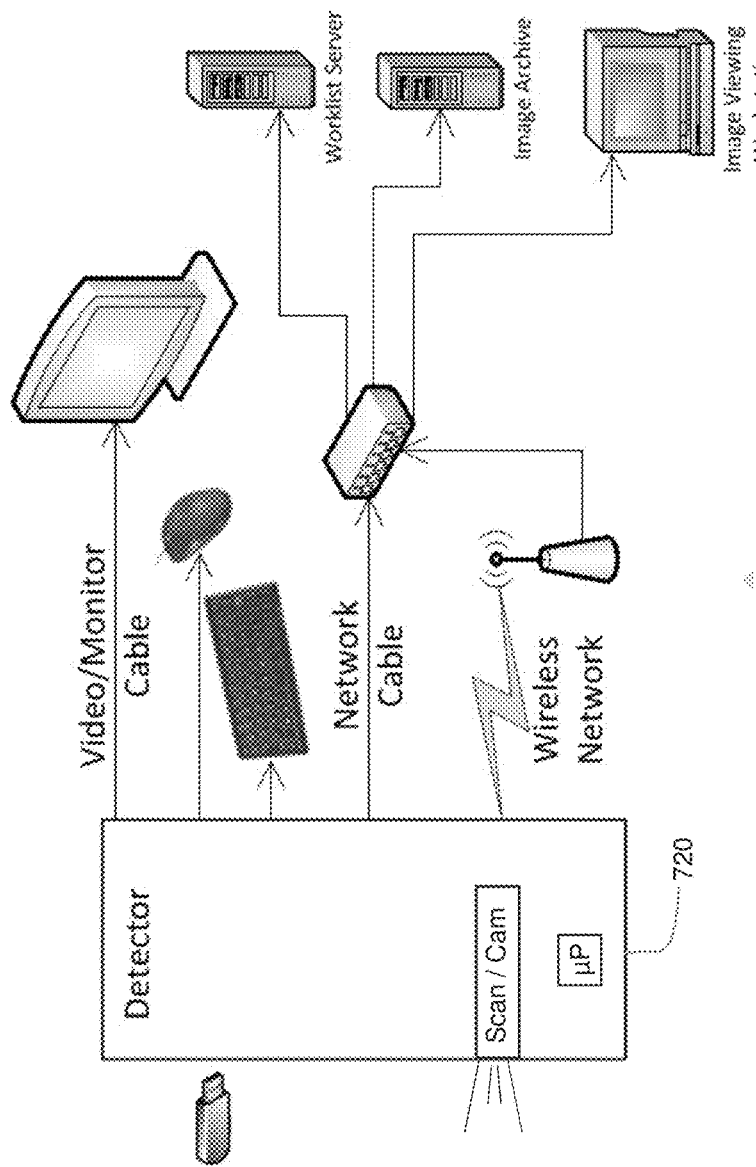
FIG. 7 is a diagram that shows an exemplary digital detector to include a display and processor at the digital detector for use as an x-ray imaging apparatus in accordance with the application.

FIG. 7 is a diagram that shows an exemplary digital detector to include a display and processor at the digital detector for use as an x-ray imaging apparatus. As shown in FIG. 7, a detector 720 comprises a DR imaging system. Thus, the detector 720 can be considered a DR imaging system. In one embodiment, the detector 720 can include functional capabilities of a mobile DR imaging system (e.g., imaging system 310). In another embodiment, the detector can include functional capabilities of just the controller 327 and console 314. Exemplary capabilities of the detector 720 can include, for example, drive a user interface on a monitor (e.g., keyboard, mouse, touch screen, or the like), exterior communication capabilities such as connecting to USB device to upload/download files, communicate wirelessly or wired to network devices and/or image acquisition control capabilities.

Figure 8:
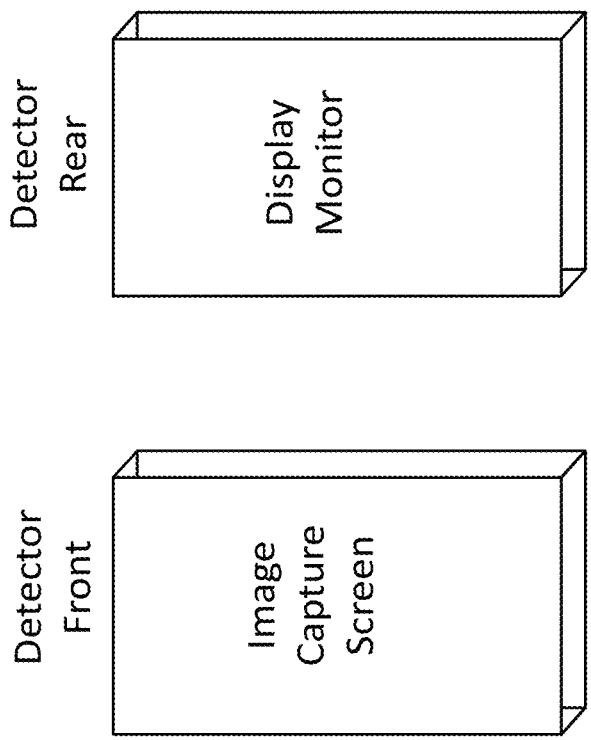
FIG. 8 is a diagram that shows another exemplary digital detector to include a display and processor at the digital detector for use as an x-ray imaging apparatus in accordance with the application.

FIG. 8 is a diagram that shows another exemplary digital detector to include a display and processor at the digital detector for use as an x-ray imaging apparatus in accordance with the application.

Figure 10:
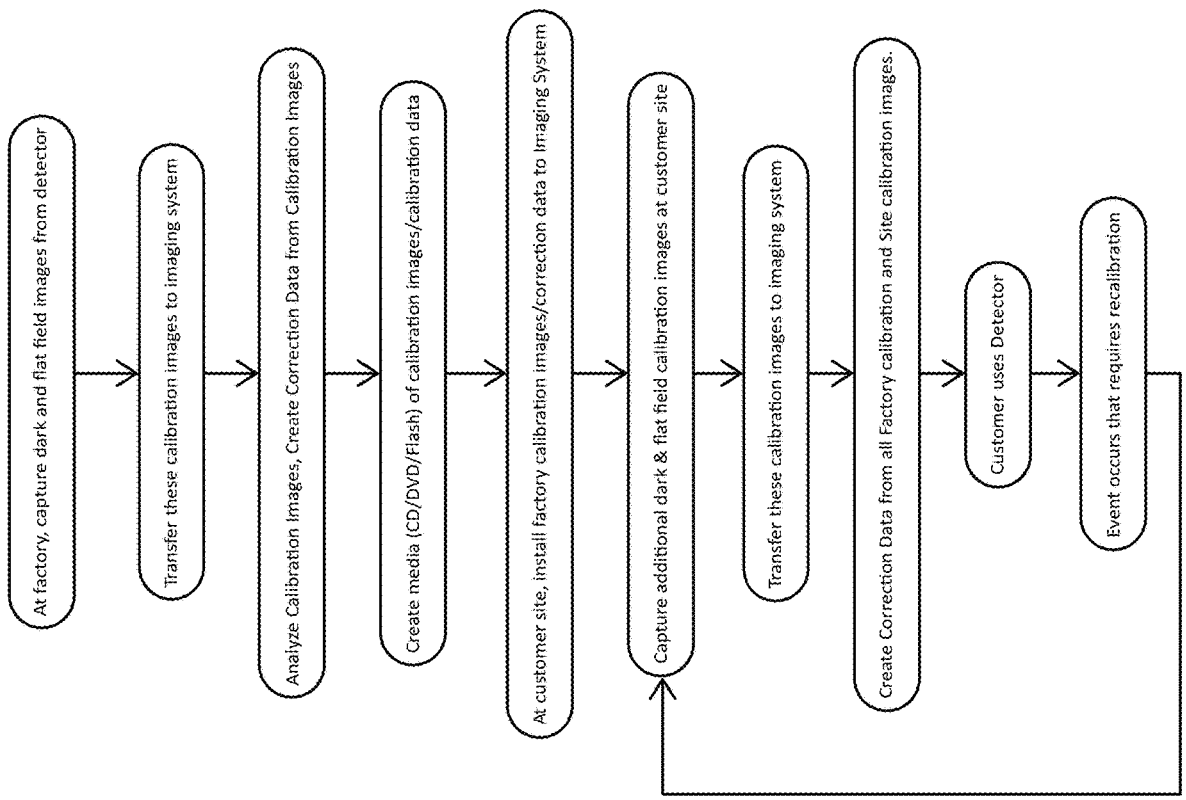
FIG. 10 is a flowchart that shows a related art image processing using calibration data at an image processor (e.g., DR console) of a radiographic imaging system.

FIG. 10 is a flowchart that shows a related art image processing using calibration data at an image processor (e.g., DR console) of a radiographic imaging system.

Figure 11:
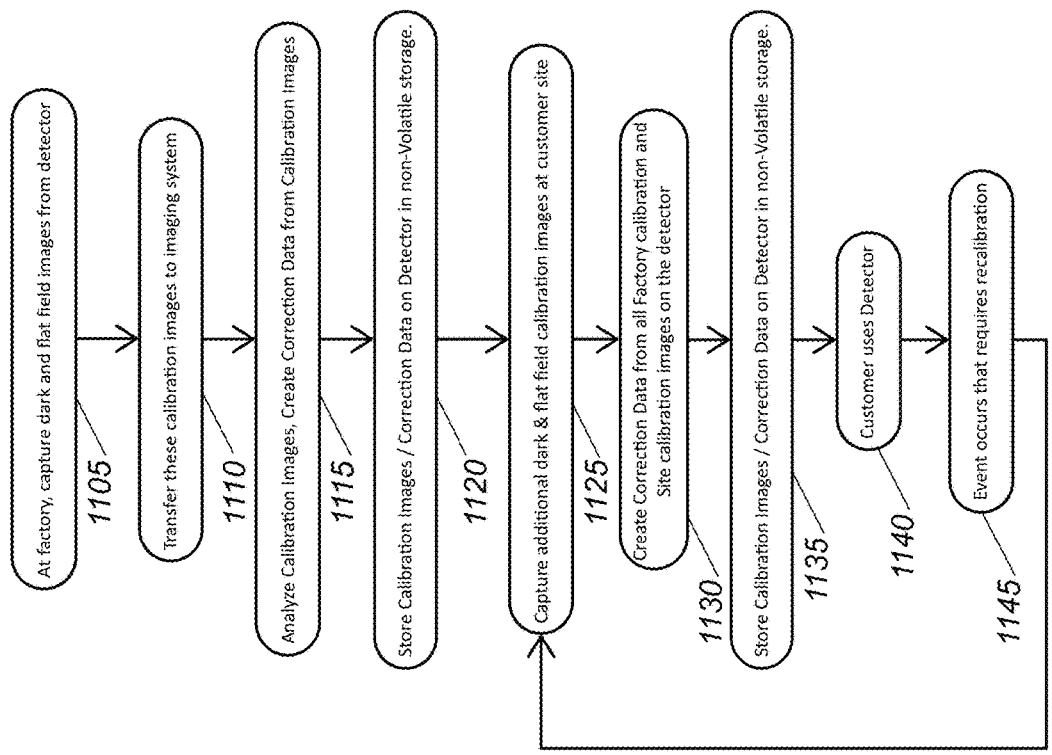
FIG. 11 is a flowchart that shows an exemplary image processing method embodiment using calibration data to correct raw image data at a DR detector of a radiographic imaging system in accordance with the application.

A method embodiment for calibrating a new portable detector will now be described. As shown in FIG. 11, first detector calibration can be calibration procedures performed initially or factory calibrations. Factory Calibration can include acquiring a large number of images (e.g., dark and flat field) with different exposure and operating characteristics of the detector (e.g., internal operating cycles of the detector, such as voltages and timing, integration times, frame rates, exposure levels, temperature) and/or exposure intervals and then saving and/or processing (e.g., averaging, combining, statistical analysis, frequency filtering, thresholding) the captured images to make a new set of images that represents the calibration maps (images). Certain exemplary embodiments can modify and/or combine the captured images or the set of calibration images so that less calibration data needs to be maintained, for example, held by the detector.

For example, taking one dark image at the detector can obtain a rough approximation of pixel offset for the detector. However, taking and averaging 100 dark images (any other integer number greater than one) can obtain a better and less noisy approximation of pixel offset for the detector. In this example, all 100 dark images may not need to be saved, but only a single averaged image can be saved.

As shown in FIG. 11, calibration data is captured at the factory (or field site) from a radiographic detector (operation block 1105). Processor logic to average 100 images can be done by the detector itself. Alternatively, averaging could be done as additional exposure characteristic data images are acquired to reduce processing time and/or memory use. Alternatively, all of the images could be transferred to a external processor such as at portable computer (PC) or imaging system console, which would perform all the logic and then transfer the calibration data (e.g., a single or smaller set of averaged or combined calibration images) back to the detector (operation block 1110). In one embodiment, this calibration data (e.g., operation block 1105, 1115, 1120) can be permanently saved for safe keeping at a remote site (e.g., manufacturer site or networked site) in case there is a memory failure of the detector in the field (e.g., removable medium or memory storing this information).

Optionally, calibration forming data (e.g., dark and/or flat field images) can be transferred from the detector to a PC, under the assumption that a PC is being used to do factory calibration analysis (operation block 1110). As shown in FIG. 11, calibration correction data can be created from the captured calibration images at the detector (operation block 1115). Exemplary calibration map generation is known to one of ordinary skill in the art of medical radiographic imaging. Then, the calibration maps (images) can be stored, for example in non-volatile memory, and preferably at the detector. In one embodiment, when the calibration maps (or a portion thereof) are not generated at the detector, the calibration correction data can be transmitted back to the detector (operation block 1120). Certain exemplary embodiments can perform all factory calibration logic at the detector, which can eliminate operation blocks 1110 and 1120.

Detector calibration can also be performed periodically or reputedly after an initial calibration (e.g., factory calibration). For example, subsequent detector calibration can be performed at a remote site or customer site. Operation blocks 1125 to 1145 can be performed at the remote site.

As shown in FIG. 11, additional calibration images (e.g., dark and/or flat field calibration images) can be acquired (operation block 1125). In operation block 1125, additional processing/logic can be performed on the calibration data to reduce time needed to acquire images. In operation block 1125, additional detector calibration can be calibration procedures performed subsequently and can include acquiring a number of additional images (e.g., dark and flat field) with different exposure or operating characteristics of the detector (e.g., internal operating cycles of the detector, such as voltages and timing, integration times, frame rates, exposure levels, temperature and/or exposure intervals and then saving and/or processing (e.g., averaging, combining, statistical analysis, frequency filtering, thresholding) the captured images to make a new set of images that represents the updated calibration maps (images).

In one embodiment, only dark images can be used to update calibration information. For example, when only a dark image(s) is used, the calibration on the detector can be performed without user intervention (e.g., the detector can initiate or perform the updated calibration automatically). For example, pre- and post-exposure dark images can be averaged to form an offset map at the time a medical examination is performed and the exposure image is acquired. Alternatively, dark calibrations can be initiated and dark images can be averaged while the detector is idle, e.g., not used with medical examination or combined with detected x-rays. Further, the final averaged dark image can be saved, preferably without saving every image that was input into the average function.

As shown in FIG. 11, the storage of acquired additional calibration information can be the actual captured images or the output of a logic processing or combining/averaging function, (e.g., that itself can look like another image). The updated calibration images and/or correction data can be stored on the detector (operation block 1135) or removable memory.

Alternatively, the images can have been transferred to a host computer PC, where the calibration processing is done, and then transfer the final calibration information is transferred back to the detector for storage (operation blocks 1130-1135).

Then, the detector can be used for radiographic imaging, preferably at medical facilities or customer locations (operation block 1140). Subsequently, an event can occur (e.g., initial registration, time elapsed, number of exposures elapsed, detector dropped, etc.), and processing can indicate that another calibration, performed by the user, is required or can automatically be performed by the detector (operation block 1145). Operation blocks 1125-1145 can be repeated.

Figure 12:
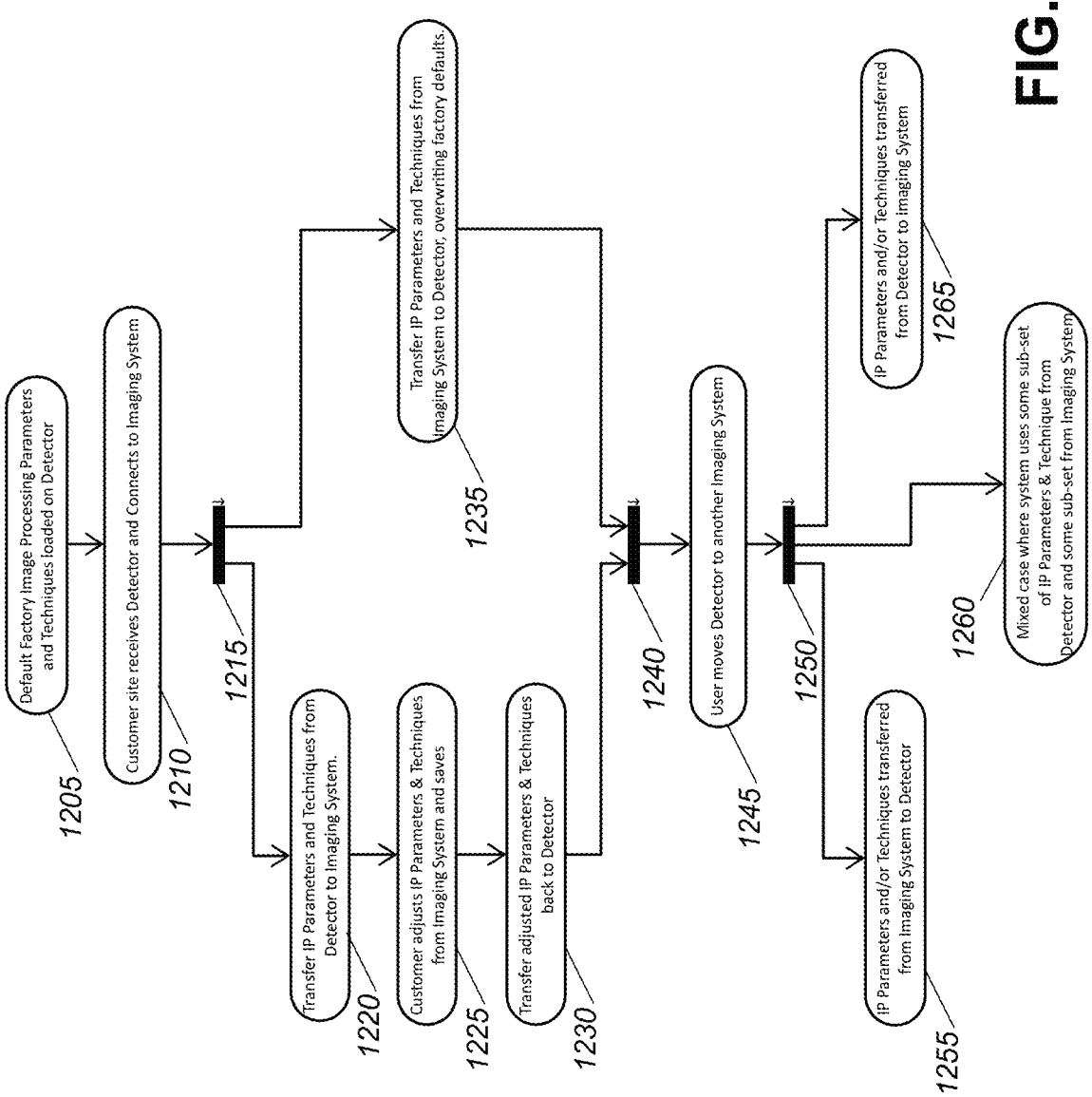
FIG. 12 is a flowchart that shows an exemplary image processing method embodiment using exposure techniques and/or calibration data at a DR detector to monitor/control/synchronize corresponding techniques in one or more radiographic imaging systems in accordance with the application.

A method embodiment for synchronizing examination procedures or exposure parameters between a radiographic detector and one or more radiographic imaging systems will now be described. In one aspect, exemplary embodiments as shown in FIG. 12 can expand on embodiments such as described with reference to FIG. 11 and store additional information at a radiographic detector to ensure consistency as the radiographic detector is moved between radiographic imaging systems. In FIG. 12, operation blocks 1215, 1240 and 1250 can be OR operations whereby the exemplary method embodiment can follow at least one of the delineated multiple paths thereafter.

As shown in FIG. 12, a first set of image processing parameters and techniques (e.g., factory parameters and techniques) can be loaded to the radiographic detector (operation block 1205). In one embodiment, the first set of factory image processing parameters and techniques can be a default set. Then, the radiographic detector is connected to (e.g., registered) to a first radiographic imaging system at an imaging site (e.g., remote or customer site) (operation block 1210). Operation block 1215 provides alternatives when a mismatch can occur between image processing parameters and techniques at the imaging system and the detector. Operation block 1215 can occur when the detector first arrives at the imaging site.

Operation blocks 1220, 1225, 1230 can address when the technician believes that the techniques and image processing parameters (TaIPP) on the detector are the correct ones (e.g., the TaIPP the technician wants to use). In this case, data for the TaIPP can be transferred from the detector to the console/imaging system PC (operation block 1220). Further, the transferred TaIPP at the console/imaging system PC can be tweaked or modified by the technician to make fine adjustments (operation block 1225). Then, the adjusted TaIPP can be transferred back up to the detector (operation block 1230).

Alternatively, the technician can believe that the techniques and image processing parameters (TaIPP) on the DR PC imaging system/console are the correct ones. In this case, the TAIPP information can be transferred from the console/imaging system PC to the detector (operation block 1235). In operation block 1235, the first set of image processing parameters and techniques can be overwritten.

In certain exemplary embodiments described herein, transferring the chosen image processing parameters (e.g., correct TaIPP) to the detector can be an optional operation unless the detector is actually performing the image processing (e.g., instead of the console/imaging system PC). Optional operations for maintaining/transferring the selected TaIPP at the detector can use the detector as a storage mechanism to move image processing parameters and techniques between radiographic imaging systems.

As shown in operation block 1240, the detector can be reused at the imaging system or another imaging system with the TaIPP stored at the detector. In certain exemplary embodiments, the detector can be transferred to another different imaging system (operation block 1245). Operation block 1250 provides alternatives when a registered detector is moved to and registered at a different imaging system whereby image processing parameters and techniques at the detector and/or the imaging system can be controlled or prioritized. Operation block 1250 can occur when the detector is registered at the different or second imaging system or subsequently.

Technicians or others can transfer techniques from a first imaging system to another second imaging system using a detector to make all of the second imaging system setup like the first imaging system setup (operation block 1265). For example, portable wireless DR detector can use differing types of scintillators (e.g., GOS, CSI), which can use differing TaIPP (e.g., different speeds, and/or differing exposure (e.g., less exposure or lower techniques) relative to one another. In one embodiment, when a technician moves a second scintillator type portable detector to an imaging system that uses only first type detectors currently, then the second scintillator type portable detector techniques and imaging can be the better data to use. Further, image processing can vary between scintillator types for portable detectors. Technicians or others can transfer techniques from a first imaging system to another second imaging system using a detector to make some or selected examinations of the second imaging system setup like the first imaging system setup (operation block 1260). In addition, when image processing is performed at the detector, then the technician does not need to transfer TaIPP from the detector to the second imaging system because the detector can operate with its own independent or current set of TaIPP, which can occur when other detectors on the second imaging system use a different set (e.g., or the imaging system uses an additional set of parameters).

Technicians or others can transfer techniques from the second imaging system to the detector to make some or selected examinations of the second imaging system setup remain consistent (operation block 1255). For example, portable wireless DR detectors can use the second imaging system TaIPP to ensure that images from the second imaging system do not appear like those from another department (e.g., ER, ICU). Accordingly, the new detector (to the second imaging system) can adapt and match operations/procedures that are is usually performed in this imaging room of the second imaging system with regards to techniques and image processing. Further, the imaging system can store imaging techniques because different grids are used at different imaging rooms whereby different techniques or imaging processing parameters at different imaging systems can be better.

Figure 13:
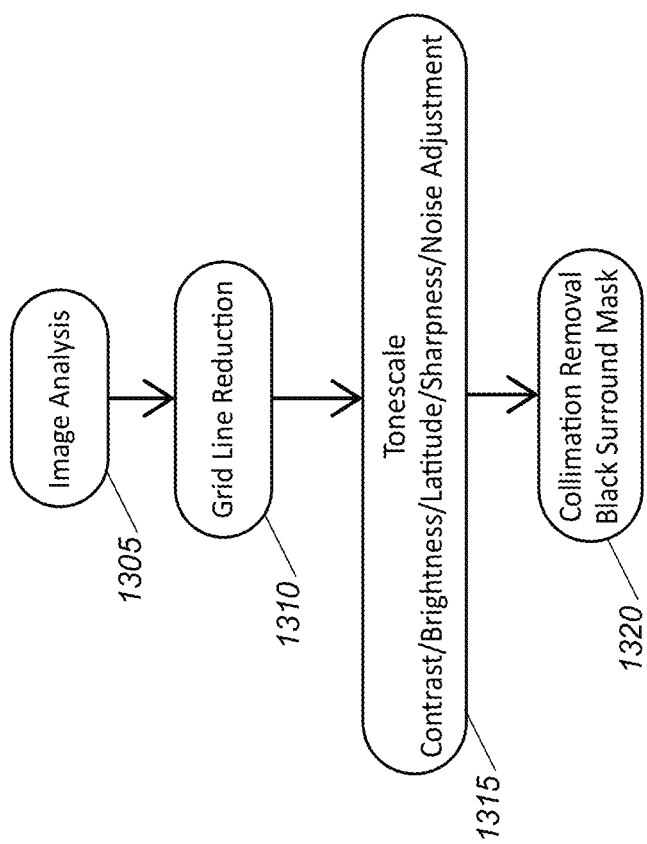
FIG. 13 is a flowchart that shows an exemplary image processing method embodiment performing additional image processing at a DR detector of a radiographic imaging system in accordance with the application.

FIG. 13 is a flowchart that shows an exemplary image processing method embodiment performing additional image processing at a DR detector of a radiographic imaging system in accordance with the application. As shown in FIG. 13, exemplary image processing can be performed (e.g., not just calibration adjustment/correction) on a radiographic detector. Exemplary types of image processing that can be performed, in whole or in part, or in various combinations are illustrated in operation blocks 1305, 1310, 1315, 1320. Exemplary image processing to be performed at the detector as shown in FIG. 13 can be considered high level example and not a complete or detailed list of image processing performed by the imaging system PC or console in related art radiographic imaging systems.

Optionally, after image processing such as but not limited to one or more of the operation block shown in FIG. 13, the detector can transfer image(s) from the detector to an imaging system console or PC, or displaying the image directly. For example, the detector can output the image only, or output the image with some meta data (e.g., describing width, height, and other necessary information) or output a DICOM image (e.g., that is a standard format to contain standardized meta data).

Certain exemplary embodiments of radiographic detector that perform image processing can vary image processing parameters based on the body part and projection being exposed. Alternatively, in less capable imaging systems or low end imaging systems, the detector can have a single image processing function for all types of images.

Alternatively, in a high end system with good image analysis, the detector may be able to process the image without being told body part/projection because the detector can determine the best image processing parameters for that particular image.

As shown in FIG. 13, the detector can process an image for presentation to the technician or user. Thus, in FIG. 13 the detector can output a processed image. As used herein, there are several definitions of a processed image. For example, usually a final presentation LUT (look-up-table) like DICOM GSDF (Grey Scale Display Functions) is applied to the image as it is displayed. In one embodiment, the method shown in FIG. 13 requires that the detector know the image processing parameters to process the image. For example, the host imaging system may also need to tell the detector what body part and projection is being used. In contrast, as shown in FIG. 11, the detector can output or produce an image (e.g., raw or calibration corrected) ready to be processed (e.g., image processed or rendered) by the imaging system console/PC.

For selected exemplary embodiment such as the all in one detector imaging system (e.g., monitor on back of detector or video cable coming out of detector, FIG. 8) then the detector can control the user interface so the detector already knows body part and projection and can itself display or output the image.

Figure 14:
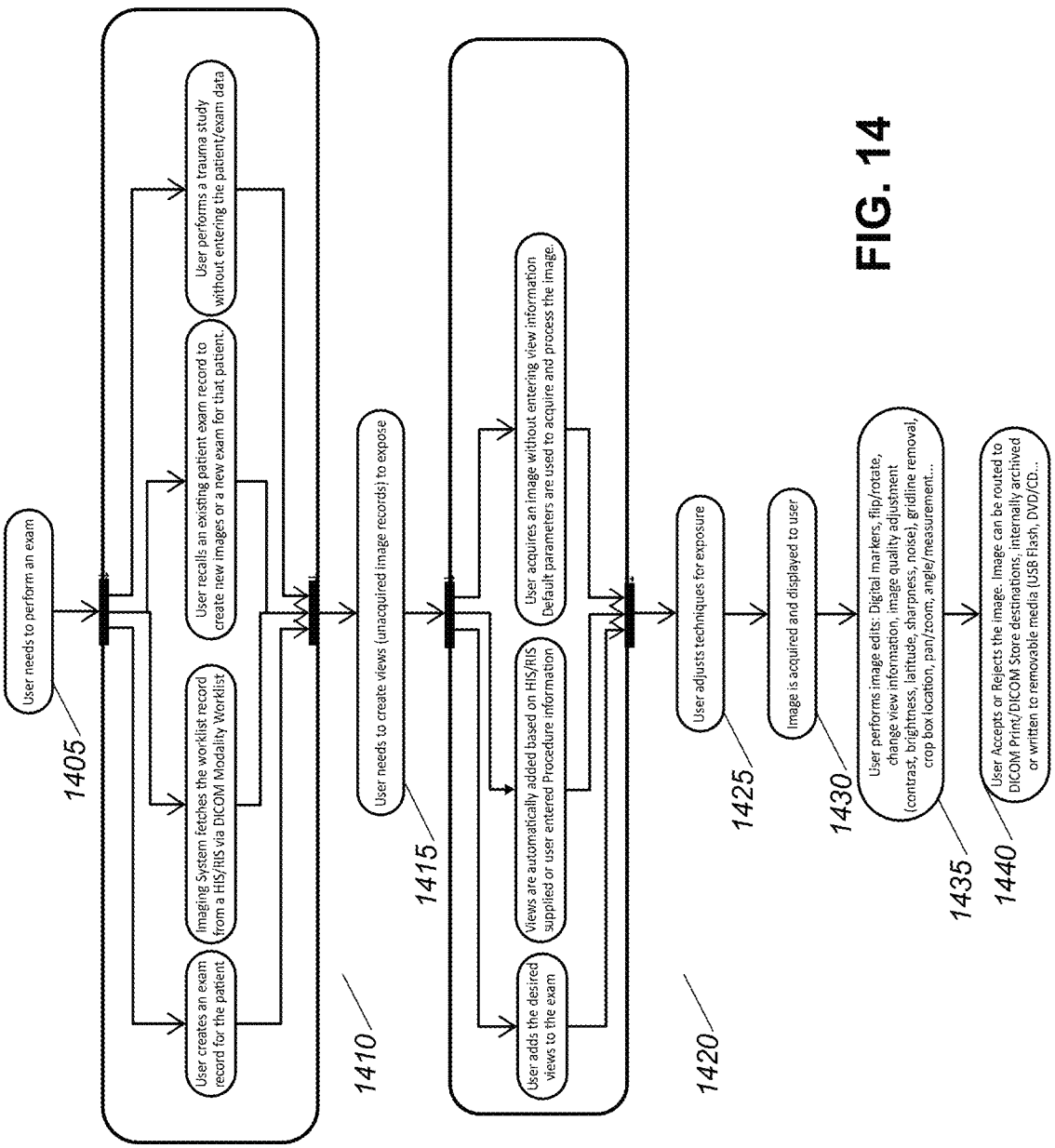
FIG. 14 is a flowchart that shows an image processing method embodiment illustrating additional exemplary operator work flow using a DR detector of a radiographic imaging system in accordance with the application.

FIG. 14 is a flowchart that shows an image processing method embodiment illustrating additional exemplary operator work flow using a DR detector being a radiographic imaging system. For example, a detector implementing operations shown in FIG. 14 can include a radiographic detector being an all in one radiographic imaging system (e.g., a display on the back of the detector with a user interface, or a video output directly on the detector to drive a slave monitor).

As shown in FIG. 14, a technician can have the detector operable to perform an exam (operation block 1405). Then, the technician can determine (e.g., create or fetch an exam) an examination to perform (operation block 1410). For example, in operation block 1410, the technician can create an examination record for a patient, recall an existing patient examination record to create new images or a new examination for the patient, the detector imaging system can fetch a worklist record for the identified technician (e.g., from a HIS/RIS via DICOM modality worklist) with examination records, or the technician can perform an examination (e.g., trauma study) without entering patient/examination data. Alternatively, the technician can receive a page or be handed a requisition form and type in the information/barcode scan the requisition form to get the examination record started. In one embodiment, patient identifying information may be printed or displayed in alphanumeric characters and/or bar code form, such as 1D or 2D bar code form, on the requisition form or on the patient's wristband, or at other places proximate a patient's location in a medical facility, such as on a patient bed, on a display screen, or on a door to a patient room. Thus, in operation clock 1410, the technician can make the examination record or the examination record can be received from elsewhere.

Returning to FIG. 7, and as described herein, the detector 720 may communicate over a network with remote or nearby processing system consoles, such as database servers, over a connected cable (wired), or the detector 720 may be equipped with a wireless transmitter/receiver to transmit captured radiographic image data wirelessly to the processing system consoles and to receive data and instructions therefrom. The detector's processor (µP) may include sufficient electronic memory to control operations of the detector, as described herein, and to store several captured radiographic images either in raw, calibrated and/or fully corrected form (e.g., gain, offset, and defect corrected). As described herein, the processor may control image transmission and image processing and image correction on board the detector based on stored programmed instructions or based on other commands transmitted and received over the network.

Still referring to FIG. 7, the detector 720 may be equipped with a scanner (Scan/Cam), such as a 1D or 2D bar code scanner, or a camera (Scan/Cam), such as a still camera or a video camera, or a combination thereof. A technician may operate the detector 720 by aiming the scanner at a bar code to receive bar coded information in the detector 720 to identify the patient. In one embodiment, a technician may aim the scanner to capture a photographic still or moving image of the patient, or a technician may aim the scanner to capture a photographic still or moving image of a bar code or of alphanumeric text associated with the patient. The processor may be programmed to receive such patient identifying information from the scanner and to display the patient identifying information on a monitor or display of the detector. The processor may be programmed to convert bar coded patient identifying information into human readable alphanumeric form for display on a monitor or display of the detector. The processor may be programmed to convert an image of alphanumeric text into corresponding digital alphanumeric characters using an optical character recognition (OCR) app stored in the detector. The processor may be programmed to recognize a photograph of the patient captured by the detector using facial recognition software to match the photograph of the patient with another previous photograph of the patient stored in a medical facility server database, wherein the detector may communicate with the medical facility server data base over a wired or wireless network access point.

The patient identifying information may be used by the processor as an index to access and retrieve additional patient information in the medical facility server database, such as from the worklist server or image archive shown in FIG. 7. The processor may be programmed to automatically access, retrieve and download the additional patient information from the medical facility servers in response to obtaining scanned and decoded patient identifying information using the scanning device. In one embodiment, the processor may be programmed to automatically display a user selectable menu on a monitor or display of the detector in response to receiving the downloaded additional patient information from the medical facility servers, whereby the user may elect from the menu which additional patient information to display on the detector's monitor or display.

The processor may be configured to display either the patient identifying information in alphanumeric form, a photograph of the patient, a radiographic image of the patient captured by the detector, or a combination thereof simultaneously, on the detector's monitor or display. Such a display may be selectably activated by a user via a user interface presented on the detector's monitor or display. Thus, radiographic images, photographs and patient information in various digital formats may be controllably processed, stored, and retrieved by the detector whether such data and information is obtained by using the scanning device in the detector or whether such data and information is downloaded from a server over a connected network.

In one embodiment, the detector may be operated to associate patient identifying information with one or a plurality of radiographic images captured by the detector. Radiographic images and the patient identifying information associated therewith may be transmitted to servers over a connected network or they may be stored on the detector for later transfer to imaging facility consoles.

Then, the technician can determine view(s) (e.g., unacquired image records) to expose (operation block 1415). As shown in operation block 1420, for example, the technician can add the desired views to the examination, views can be automatically added to the examination based on HIS/RIS or user supplied information, or the technician can acquire an image(s) without entering view information. Thus, in operation clock 1420, the technician can make the views (e.g., images to expose) record or the views can be automatically created/received from elsewhere.

Then, if selected, the technician can adjust the techniques (operation block 1425). In one embodiment (e.g., in room DR imaging system), the technician can control the techniques from a user interface (UI), which means the detector can be in direct contact with the x-ray generator and the prep/expose logic. Alternatively, for a retrofit radiographic imaging system, the technician can change techniques on the generator hardware, which may or may not be integrated with the detector. In addition, where the detector can be remotely accessed by a GUI drive imaging system console or PC), the detector also can be remotely controlled by a remote desktop connection or the like (e.g., tablet PC). In one embodiment, the detector can use a network connection for remote control and/or video like remote desktop or net meeting or remote PC control applications.

After the image is acquired, the acquired image can be shown to the technician on the monitor on the detector or on a remote display controlled by the detector (operation block 1430). In one embodiment, a full sized monitor on the back of the detector can display the acquired image where the displayed image is the same exact size as the acquired image or the detector that captured the image (e.g., see FIG. 8).

Then, the acquired image can be manipulated by the technician (operation block 1435) and accepted/rejected by the technician (operation block 1440). Further, acquired images (e.g., accepted or rejected, etc.) be stored locally, remotely or to a removable medium. In one embodiment, to deliver the image to the hospital's PACS system a wired or wireless connection can be used.

In a military use case or a field use situation, it is the technician at the remote site that needs to see the image. No system to deliver to, but the technician can save the image on the detector for later transfer to a PACS upon return from the filed or remote site. Alternatively, a supplemental long distance wireless communication method (e.g., satellite or cell phone technology) to send an image back to home base for evaluation by another technician or professional doctor.

Certain exemplary embodiments herein provide methods and/systems that can perform calibration image processing (e.g., one or more corrections including but not limited to dark correction or offset correction, gain correction, defect correction) that can include (i) forming calibration data, calibration images or calibration maps at the detector or fair use at the detector, or (ii) correcting (e.g., raw image) images of objects by applying calibration data, calibration images or calibration maps to such images of objects acquired by the detector (or elsewhere). Thus, exemplary embodiments herein can provide methods and/systems that can perform calibration file updates or calibration procedures that result in calibration files and/or information used in correcting subsequent raw radiographic image data at a radiographic detector. Further, additional image processing (e.g., image rendering) can be performed by a digital detector of radiographic image systems.

In one embodiment, calibration can be divided into two categories: factory and site calibration. Factory calibration is performed (e.g., by manufacturer) prior to shipping the detector for use (e.g., to the customer). Factor calibration data (e.g., images) are usually geared toward that which will not change over the life of the detector. For example, the calibration information can be valid regardless of detector temperature, how many images have been exposed, age of detector, etc. Factory calibration can use an automated process and the factory calibration can involve more images than site calibration.

Related art calibration data can provided by a DVD with many calibration images with the detector. Then, the technician must load the images on the DVD to any radiographic imaging system that will use the detector.

Certain exemplary embodiments here can send the detector with this calibration data on the detector itself and correct the images on the detector, so that there is no need to spend time (e.g., minutes) transferring these calibration data to each imaging system that can use the detector.

Once the detector is registered to a specific radiographic imaging system for use, the imaging system can determine that the required periodic (e.g., repeated) site calibration has not been performed on that imaging system. Site calibration can include daily, weekly, monthly, yearly, or every 100 images . . . type of calibration. Site correction can address properties of the detector that could change or drift over time. Site calibration can address a dropped detector because that action can cause the glass or substrate to shift and invalidate any current calibration. In related art imaging systems, because site calibration isn't on the DVD with calibration images, unique site calibration is performed on every DR imaging system to which the detector is registered. Accordingly, site calibrations are effectively required over and over on each imaging system.

For example, a radiography department has three rooms and a selected detector is primarily in room 1 and only registered with rooms 2 and 3 as a backup detector. Further, room 2 does not use the selected detector until 6 months later whereby all of the periodic calibrations for the selected detector have expired on the room 2 imaging system. At that point, in related art imaging systems, the technician can be required to perform daily, weekly, monthly, and maybe longer periodic calibrations on the selected detector (which may take up to an hour) before the selected detector can be used in room 2. However, the site calibrations are up to date for the selected detector on the room 1 imaging system.

As used herein, controller/CPU for the detector panel (e.g., detector 12) or imaging system (controller 34 or 327) also includes an operating system (not shown) that is stored on the computer-accessible media RAM, ROM, and mass storage device, and is executed by processor. Examples of operating systems include Microsoft Windows®, Apple MacOS®, Linux®, UNIX®. Examples are not limited to any particular operating system, however, and the construction and use of such operating systems are well known within the art. Embodiments of controller/CPU for the detector (e.g., detector 12) or imaging system (controller 34 or 327) are not limited to any type of computer. In varying embodiments, controller/CPU comprises a PC-compatible computer, a MacOS®-compatible computer, a Linux®-compatible computer, or a UNIX®-compatible computer. The construction and operation of such computers are well known within the art. The controller/CPU can be operated using at least one operating system to provide a graphical user interface (GUI) including a user-controllable pointer. The controller/CPU can have at least one web browser application program executing within at least one operating system, to permit users of the controller/CPU to access an intranet, extranet or Internet world-wide-web pages as addressed by Universal Resource Locator (URL) addresses. Examples of browser application programs include Netscape Navigator® and Microsoft Internet Explorer®.

In some embodiments, exemplary methods can be implemented as a computer data signal embodied in a carrier wave, that represents a sequence of instructions which, when executed by a processor, such as processor 34, 327, can cause the processor to perform the respective method. In other embodiments, exemplary methods can be implemented as a computer-accessible medium having executable instructions capable of directing a processor, such as processor 34, 327, to perform the respective method. In varying embodiments, the medium is a magnetic medium, an electronic medium, or an optical medium.

The present application uses the term "imaging room" or more simply "room" as it is conventionally used and understood by those practiced in the radiology arts, to apply to an installation of an x-ray imaging apparatus or system at a specific location that has one or more DR receiver panels that can be assigned to that system. There is generally an organizational hierarchy for x-ray rooms in a given facility. One or more imaging rooms may be grouped together as part of a "department" within a hospital or other facility in which x-rays are obtained. For example, the emergency room may be considered as a department and may itself have two or more rooms for x-ray imaging. There may then be a number of departments within a hospital or other care facility, which is generally termed a "site" or "facility" in the context of the present disclosure. Problems addressed by embodiments of the application can of particular relevance where a hospital or other type of site has multiple departments for DR radiological imaging and more particularly where each department can have multiple rooms or DR detectors assigned as floating DR detectors.

Radiographic detectors can be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation.

Refer also to commonly assigned US Published Patent Application 20100020933, which is hereby incorporated by reference.

It should be noted that the present teachings are not intended to be limited in scope to the embodiments illustrated in the figures.

While the invention has been illustrated with respect to one or more implementations, alterations and/or modifications can be made to the illustrated examples without departing from the spirit and scope of the appended claims. For example, the various pixel embodiments can be used in radiation imaging systems. An example radiation imaging system can include a plurality of the various pixel embodiments in an array, driving circuits, readout circuits, and a phosphor screen. A radiation source can also be included.

In addition, while a particular feature of the invention have been disclosed with respect to only one of several implementations, such feature can be combined with one or more other features of the other implementations as can be desired and advantageous for any given or particular function. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected.

In one embodiment, a method for operating a radiographic imaging system, the method comprising operably coupling a portable detector to the imaging system, wherein the portable detector comprises a memory to store calibration data; correcting image data using the stored calibration data; and transmitting a calibration data corrected image to the radiographic imaging system.

In one embodiment, an apparatus for a radiographic imaging system comprising: a detector storing calibration data; a transmit and receive unit for external communication; and a detector controller to respond to incident radiation to transmit a calibration data corrected image through said transmit and receive unit.

In one embodiment, a detector for a radiographic imaging system comprising: a memory comprising calibration data, and configuration data; a. transmit and receive unit for communicating with the radiographic imaging system; and a detector controller responding to a request for identification of said detector received through said transmit and receive unit and transmitting an ID from said memory to the radiographic imaging system.

In one embodiment, a system for obtaining an x-ray image comprising: a plurality of x-ray imaging systems, each x-ray imaging system comprising at least one x-ray generator; and at least one at least one portable digital radiography detector to store image exposure technique information, wherein the technique information is used with the portable DR detector at one or more radiographic imaging systems. In the system a plurality of x-ray imaging systems are coupled to an imaging system network, wherein the image exposure technique information comprises comprise at least one of kVp, mAs, ma, time, or AEC configuration.

In one embodiment, the detector comprises memory including one or more cache, ROM, PROM, EPROM, EEPROM, flash, SRAM, non-volatile memory (NVM), flash memory and removable memory, and wherein the imaging system is a portable imaging system, wherein calibration data comprises factory calibration files, wherein the memory comprises configuration data.

In one embodiment, wherein the detector is identified to the radiographic itna.ging system by manual physical connection and a manual operator action, wherein required information is transferred from the detector to the radiographic imaging system after the detector is identified, wherein the required information comprises one or more of unique ID, a serial number, an IP address, a name, a detector type, width/height in prescribed dimension units, width/height in pixels, detector type (GOS, CSI) and not calibration data and, wherein the detector is selected or activated to the radiographic imaging system by manual physical connection and a manual operator action.

In one embodiment, an apparatus for a radiographic imaging system can include a detector including an image receptor to receive incident x-ray radiation and generate electronic image data; a storage device configured to store image processing parameters; and a processor configured to perform image processing at the detector from the electronic image data and the image processing parameters.

The apparatus can include image processing parameters that are view based image processing parameters, the processor to store processing data for each view. The at least one view can include body part, projection, position, or a combination thereof.

The apparatus can further include a plurality of different radiographic imaging systems, the detector to store view information, image processing parameters or exposure techniques for use with the radiographic imaging system, the detector to transfer the view information, image processing parameters or exposure techniques from a first radiographic imaging systems to a second radiographic imaging system.

The apparatus can perform image processing at the detector, technique information is stored at the detector, wherein the technique information is used with the detector at one or more radiographic imaging systems.

In one embodiment, the detector can synchronize view information, image processing parameters or exposure techniques with the imaging system upon connection, wherein the connection is a wireless connection or physical connection, a hot swap operation or a detector registration, the detector to receive the view information, image processing parameters or exposure techniques from an initial radiographic imaging system, at the factory or at an initialization operation.

In one embodiment, the detector to transfer view information, image processing parameters or exposure techniques from a first radiographic imaging systems to a second radiographic imaging system.

In one embodiment, the detector to store exposure techniques, wherein exposure techniques comprise at least one of kVp, mAs, ma, time, or AEC configuration, where the exposure techniques are transmitted to a generator before the incident radiation is received.

In one embodiment, detector is to transmit multiple copies of a first image to the imaging system, where the multiple copies of the first image comprise raw image data, calibration corrected image data, or processed image data, where the multiple copies of the first image reduce operator preview times, where the multiple copies of the first image are transmitted over a network or the interact, where the multiple copies of the first image comprise a preview image or the multiple copies of the first image are full, sampled or reduced images. Further, the detector is configured to produce fully processed image data or to produce image data for display to an operator.

The apparatus can include a display, monitor or a remote desktop or web application to couple to the detector, where the display is wirelessly connected to the detector or directly connected to the detector with a cable and a connector, where the connector comprises a DVI, HDMI mini-HDMI, Display Port, a prescribed connector, a customized connector, or mini-Display Port connector.

In one embodiment, the detector can include a first surface and an opposite surface, where the second surface comprises a display to display the calibration data corrected image. Further, the flat panel display can be a touch screen display to display raw image data, calibration corrected image data or processed images, where the detector comprises the radiographic imaging system, where the flat panel display is a touch screen display to display DICOM images or x-ray image data including patient and examination procedure information. Alternatively, the flat panel display can perform DR console operations for digital radiographic imaging room systems or digital radiographic imaging mobile systems.

The apparatus can configure the detector to satisfy milspec requirements for durability, reliability, robustness, military hardened electronic equipment or battlefield operations.

In one embodiment, the processor at the detector can perform additional image processing before transmitting the corrected image to the radiographic imaging system, the additional image processing comprising at least one of compensation processing, expansion/compression processing, space filtering processing, recursive processing, gradation processing, scattering radiation compensation processing, grid compensation processing, frequency enhancement processing, dynamic range compression processing, noise suppression, or tone scaling comprising contrast, brightness, latitude, noise or sharpness.

In one embodiment, the detector is configured to access patient information and examination procedure information, the detector to transmit DICOM images or x-ray image data including patient and examination procedure header information.

Further, in the discussion and claims herein, the term "about" indicates that the value listed can be somewhat altered, as long as the alteration does not result in nonconformance of the process or structure to the illustrated embodiment. In addition, while a particular feature of the invention can have been disclosed with respect to only one of several implementations, such feature can be combined with one or more other features of the other implementations as can be desired and advantageous for any given or particular function. The term "at least one of" is used to mean one or more of the listed items can be selected. Also, "exemplary" indicates the description is used as an example, rather than implying that it is an ideal.

The invention claimed is:

1. A portable digital radiographic detector comprising:
an array of imaging pixels on a front side of the detector to capture a radiographic image;
a display on a back side of the detector opposite the front side;
a processor and memory configured to store the captured radiographic image;
a scanning device configured to scan patient identifying information and to electronically store patient identifying information as digital alphanumeric characters generated from the scanned patient identifying information, wherein the processor is further configured to associate the stored digital alphanumeric character patient identifying information with the captured radiographic image; and
a housing to at least partially enclose the array of imaging pixels, the display, the processor and the scanning device,
wherein the processor is further configured to simultaneously display the stored digital alphanumeric characters and the captured radiographic image on the display.

2. The detector of claim 1, wherein the scanning device comprises a 1D barcode scanner, a 2D barcode scanner, a digital video camera, a digital still image camera or a combination thereof.

3. The detector of claim 2, wherein the patient identifying information comprises a still or a moving image, the still or moving image comprises an image of the patient, an image of a requisition form, an image of a room number, or a combination thereof.

4. The detector of claim 1, further comprising a transmitter configured to wiredly or wirelessly transmit the captured radiographic image and the patient identifying information associated therewith.

5. The detector of claim 4, wherein the processor is further configured to automatically wiredly or wirelessly communicate the patient identifying information over a connected network in order to access and retrieve from a server additional information about a patient corresponding to the patient identifying information.

6. The detector of claim 5, wherein the additional patient information comprises a photograph of the corresponding patient, a health history of the corresponding patient, a radiographic image history of the corresponding patient, an imaging exam schedule for the corresponding patient or a combination thereof, and wherein the display is further configured to display the additional patient information.

7. The detector of claim 6, wherein the processor is further configured to associate the additional patient information with the captured radiographic image and to wiredly or wirelessly communicate the captured radiographic image and the additional patient information to the server.

8. A method of operating a portable digital radiographic detector comprising an array of imaging pixels on a front side of the detector, a display on a back side of the detector, and a scanning device, the method comprising:
scanning patient identifying information using the scanning device;
capturing a radiographic image of a patient associated with the patient identifying information;
generating digital alphanumeric characters based on the scanned patient identifying information, and electronically storing the digital alphanumeric characters;
simultaneously displaying the stored digital alphanumeric characters and the captured radiographic image of the patient on the display; and
obtaining additional information corresponding to the patient identifying information and displaying the obtained additional information on the display.

9. The method of claim 8, further comprising transmitting the captured radiographic image of the patient together with the patient identifying information associated therewith.

10. The method of claim 8, further comprising displaying a user interface on the display and receiving a user input therefrom to selectively display the captured radiographic image of the patient, the digital alphanumeric characters, or both.

11. The method of claim 10, wherein the step of scanning patient identifying information comprises scanning a 1D barcode, scanning a 2D barcode, capturing a digital video image, capturing a digital still image, or a combination thereof.

12. The method of claim 11, wherein the step of scanning patient identifying information further comprises capturing a digital still image or digital video image of the patient, of a requisition form, of a room number, or a combination thereof.

13. The method of claim 12, further comprising the detector automatically wiredly or wirelessly communicating the patient identifying information over a connected network and receiving from a server the additional information corresponding to the patient identifying information.

14. The method of claim 13, further comprising receiving from the server a photograph of the corresponding patient, a health history of the corresponding patient, a radiographic image history of the corresponding patient, an imaging exam schedule for the corresponding patient or a combination thereof, in response to the step of communicating the patient identifying information over the connected network.

* * * * *